US006524851B1

(12) United States Patent
Ellis

(10) Patent No.: US 6,524,851 B1
(45) Date of Patent: Feb. 25, 2003

(54) HYBRID NUCLEIC ACID MOLECULES AND VECTORS INCLUDING β-GLOBIN REGULATORY ELEMENTS

(75) Inventor: James Ellis, Toronto (CA)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 09/411,449

(22) Filed: Oct. 1, 1999

(30) Foreign Application Priority Data

Oct. 1, 1998 (CA) ........................................ 2246005

(51) Int. Cl.[7] .......................... C12N 15/00; C12N 15/63

(52) U.S. Cl. .................... 435/325; 435/69.1; 435/91.4; 435/320.1; 435/455

(58) Field of Search .............................. 536/24.1, 23.1, 536/23.5; 435/320.1, 325, 455

(56) References Cited

U.S. PATENT DOCUMENTS 6,022,738 A * 2/2000 Atweh .................... 435/320.1

FOREIGN PATENT DOCUMENTS

| WO | 94-29470 | * 12/1994 |
|---|---|---|
| WO | 95-04744 | * 2/1995 |

OTHER PUBLICATIONS

Ngo et al., Computational Complexity Protein Structure Prediction and the Levinthal Pradox, 1994, Birkhauser Boston, pp. 492–495.*

TIG, 1996, vol. 12, No. 12, pp. 496–497.*

Navas et al., 1995, Gene 160:165–171.

Aladjem, Mirit I., Rodewald, Luo Wei et al., "Genetic Dissection of a Mammalian Replicator in the Human β–Globin Locus", *Science*, 281: 1005–1009 (1998).

Ellis, James, Pasceri, Peter et al., "Evaluation of β–globin therapy constructs in single copy transgenic mice", *Nucleic Acids Research*, 25: 1296–1302 (1997).

Ellis, James, Tan–Un2, Kian C. et al., "A dominant chromatin–opening in 5' hypersensitive site 3 of the human β–globin locus control region", *The EMBO Journal*, 15: 562–568 (1996).

Emery, D. W., Chen, H., Li, Q. et al., "Development of a condensed locus control region cassette and testing in retrovirus sectors for $^{A}\gamma$–globin", *Blood Cells, Molecules and Diseases*, 24: 322–339 (1998).

Li, Q., Emery, D. W., Fernandez, M. et al., "Development of viral vectors for gene therapy of β–chain hemoglobinopathies: optimization of a γ–globin gene expression cassette", *Blood*, 93: 2208–2216 (1999).

McCune, S.L., Reilly, M.P., Chomo, M.J. et al., "Recombinant human hemoglobins designed for gene therapy of sickle cell disease", *Proc. Natl. Acad Sci USA*, 91: 9852–9856 (1994).

Pasceri, P., Pannell, D., Wu, X. et al., "Full activity from human β–globin locus control region transgenes requires 5'HS1, distal β–globin promoter, and 3' β–globin sequences", *Blood*, 92: 653–663 (1998).

Takekoshi, K.J., Young, H.O., Westerman, K.W. et al., "Retroviral transfer of a human β–globin / δ–globin hybrid gene linked to β locus control region hypersensitive site 2 aimed at the gene therapy of sickle cell disease", *Proc Nat Acad Sci USA*, 92: 3014–3018 (1995).

Trudel, M., Costantini, F., "A 3' enhancer contributes to the stage–specific expression of the human β–globin gene", *Genes& Development*, 1: 954–961 (1987).

Trudel, M., Magram, J., Bruckner, L. et al., "Upstream Gγ–globin and downstream β–globin sequences required for stage–specific expression in transgenic mice", *Molecular and Cellular Biology*, 7: 4024–4029 (1987).

* cited by examiner

*Primary Examiner*—Dave T. Nguyen
(74) *Attorney, Agent, or Firm*—Cheryl H. Agris

(57) ABSTRACT

The invention relates to hybrid nucleic acid molecules for gene therapy in cells of the erythroid lineage, and in particular α-, β-, δ-, ϵ, γ-, or ζ-globin nucleotide sequences operably linked to β-globin regulatory elements. The hybrid nucleic acid molecules, at single copy, are capable of producing a polypeptide. The hybrid nucleic acid molecules are useful for treatment of hemoglobinopathies such as sickle cell anemia or β-thalassemia.

The hybrid nucleic acid molecules are useful at single copy for erythroid expression at single copy of RNA and polypeptides in transgenic animals.

16 Claims, 48 Drawing Sheets

| FIG.8A-1 |
| --- |
| FIG.8A-2 |
| FIG.8A-3 |
| FIG.8A-4 |
| FIG.8A-5 |
| FIG.8A-6 |
| FIG.8A-7 |
| FIG.8A-8 |
| FIG.8A-9 |

SEQ ID NO.: 1
Without Aγ-globin coding sequence

```
      ClaI          XhoI
      ~~~~         ~~~~~~
 15   CGATGAAGCT TCCTCGAGGC AGAAGAGTCA AGCATTTGCC TAAGGTCGGA
      GCTACTTCGA AGGAGCTCCG TCTTCTCAGT TCGTAAACGG ATTCCAGCCT
-------------------------------------------------------------
 65   CATGTCAGAG GCAGTGCCAG ACCTATGTGA GACTCTGCAG CTACTGCTCA
      GTACAGTCTC CGTCACGGTC TGGATACACT CTGAGACGTC GATGACGAGT
-------------------------------------------------------------
115   TGGGCCCTGT GCTGCACTGA TGAGGAGGAT CAGATGGATG GGGCAATGAA
      ACCCGGGACA CGACGTGACT ACTCCTCCTA GTCTACCTAC CCCGTTACTT
-------------------------------------------------------------
165   GCAAAGGAAT CATTCTGTGG ATAAAGGAGA CAGCCATGAA GAAGTCTATG
      CGTTTCCTTA GTAAGACACC TATTTCCTCT GTCGGTACTT CTTCAGATAC
-------------------------------------------------------------
215   ACTGTAAATT TGGGAGCAGG AGTCTCTAAG GACTTGGATT TCAAGGAATT
      TGACATTTAA ACCCTCGTCC TCAGAGATTC CTGAACCTAA AGTTCCTTAA
-------------------------------------------------------------
265   TTGACTCAGC AAACACAAGA CCCTCACGGT GACTTTGCGA GCTGGTGTGC
      AACTGAGTCG TTTGTGTTCT GGGAGTGCCA CTGAAACGCT CGACCACACG
-------------------------------------------------------------
315   CAGATGTGTC TATCAGAGGT TCCAGGGAGG GTGGGGTGGG GTCAGGGCTG
      GTCTACACAG ATAGTCTCCA AGGTCCCTCC CACCCCACCC CAGTCCCGAC
-------------------------------------------------------------
```

```
365  GCCACCAGCT ATCAGGGCCC AGATGGGTTA TAGGCTGGCA GGCTCAGATA
     CGGTGGTCGA TAGTCCCGGG TCTACCCAAT ATCCGACCGT CCGAGTCTAT
------------------------------------------------------------
415  GGTGGTTAGG TCAGGTTGGT GGTGCTGGGT GGAGTCCATG ACTCCCAGGA
     CCACCAATCC AGTCCAACCA CCACGACCCA CCTCAGGTAC TGAGGGTCCT
------------------------------------------------------------
465  GCCAGGAGAG ATAGACCATG AGTAGAGGGC AGACATGGGA AAGGTGGGGG
     CGGTCCTCTC TATCTGGTAC TCATCTCCCG TCTGTACCCT TTCCACCCCC
------------------------------------------------------------
515  AGGCACAGCA TAGCAGCATT TTTCATTCTA CTACTACATG GGACTGCTCC
     TCCGTGTCGT ATCGTCGTAA AAAGTAAGAT GATGATGTAC CCTGACGAGG
------------------------------------------------------------
565  CCTATACCCC CAGCTAGGGG CAAGTGCCTT GACTCCTATG TTTTCAGGAT
     GGATATGGGG GTCGATCCCC GTTCACGGAA CTGAGGATAC AAAAGTCCTA
------------------------------------------------------------
615  CATCATCTAT AAAGTAAGAG TAATAATTGT GTCTATCTCA TAGGGTTATT
     GTAGTAGATA TTTCATTCTC ATTATTAACA CAGATAGAGT ATCCCAATAA
------------------------------------------------------------
665  ATGAGGATCA AAGGAGATGC ACACTCTCTG GACCAGTGGC CTAACAGTTC
     TACTCCTAGT TTCCTCTACG TGTGAGAGAC CTGGTCACCG GATTGTCAAG
------------------------------------------------------------
715  AGGACAGAGC TATGGGCTTC CTATGTATGG GTCAGTGGTC TCAATGTAGC
     TCCTGTCTCG ATACCCGAAG GATACATACC CAGTCACCAG AGTTACATCG
------------------------------------------------------------
765  AGGCAAGTTC CAGAAGATAG CATCAACCAC TGTTAGAGAT ATACTGCCAG
     TCCGTTCAAG GTCTTCTATC GTAGTTGGTG ACAATCTCTA TATGACGGTC
```

FIG.8A-2

```
815   TCTCAGAGCC TGATGTTAAT TTAGCAATGG GCTGGGACCC TCCTCCAGTA
      AGAGTCTCGG ACTACAATTA AATCGTTACC CGACCCTGGG AGGAGGTCAT
-----------------------------------------------------------
                          XhoI      SpeI     KpnI  SalI
                        ~~~~~~~   ~~~~~~   ~~~~~~~~~~~~~
865   GAACCTTCTA ACCAGCCTCG AGGGACTAGT CGGTACCGTC GACAACCTCC
      CTTGGAAGAT TGGTCGGAGC TCCCTGATCA GCCATGGCAG CTGTTGGAGG
-----------------------------------------------------------
915   TATTTGACAC CACTGATTAC CCCATTGATA GTCACACTTT GGGTTGTAAG
      ATAAACTGTG GTGACTAATG GGGTAACTAT CAGTGTGAAA CCCAACATTC
-----------------------------------------------------------
965   TGACTTTTTA TTTATTTGTA TTTTTGACTG CATTAAGAGG TCTCTAGTTT
      ACTGAAAAAT AAATAAACAT AAAAACTGAC GTAATTCTCC AGAGATCAAA
-----------------------------------------------------------
1015  TTTATCTCTT GTTTCCCAAA ACCTAATAAG TAACTAATGC ACAGAGCACA
      AAATAGAGAA CAAAGGGTTT TGGATTATTC ATTGATTACG TGTCTCGTGT
-----------------------------------------------------------
1065  TTGATTTGTA TTTATTCTAT TTTTAGACAT AATTTATTAG CATGCATGAG
      AACTAAACAT AAATAAGATA AAAATCTGTA TTAAATAATC GTACGTACTC
-----------------------------------------------------------
1115  CAAATTAAGA AAAACAACAA CAAATGAATG CATATATATG TATATGTATG
      GTTTAATTCT TTTTGTTGTT GTTTACTTAC GTATATATAC ATATACATAC
-----------------------------------------------------------
1165  TGTGTATATA TACACATATA TATATATATT TTTTTTCTTT TCTTACCAGA
      ACACATATAT ATGTGTATAT ATATATATAA AAAAAAGAAA AGAATGGTCT
-----------------------------------------------------------
1215  AGGTTTTAAT CCAAATAAGG AGAAGATATG CTTAGAACTG AGGTAGAGTT
      TCCAAAATTA GGTTTATTCC TCTTCTATAC GAATCTTGAC TCCATCTCAA
-----------------------------------------------------------
```

FIG.8A-3

```
1265  TTCATCCATT CTGTCCTGTA AGTATTTTGC ATATTCTGGA GACGCAGGAA
      AAGTAGGTAA GACAGGACAT TCATAAAACG TATAAGACCT CTGCGTCCTT

1315  GAGATCCATC TACATATCCC AAAGCTGAAT TATGGTAGAC AAAGCTCTTC
      CTCTAGGTAG ATGTATAGGG TTTCGACTTA ATACCATCTG TTTCGAGAAG

1365  CACTTTTAGT GCATCAATTT CTTATTTGTG TAATAAGAAA ATTGGGAAAA
      GTGAAAATCA CGTAGTTAAA GAATAAACAC ATTATTCTTT TAACCCTTTT

                                                 SnaBI
                                               ~~~~~~~
1415  CGATCTTCAA TATGCTTACC AAGCTGTGAT TCCAAATATT ACGTAAATAC
      GCTAGAAGTT ATACGAATGG TTCGACACTA AGGTTTATAA TGCATTTATG

1465  ACTTGCAAAG GAGGATGTTT TTAGTAGCAA TTTGTACTGA TGGTATGGGG
      TGAACGTTTC CTCCTACAAA AATCATCGTT AAACATGACT ACCATACCCC

1515  CCAAGAGATA TATCTTAGAG GGAGGGCTGA GGGTTTGAAG TCCAACTCCT
      GGTTCTCTAT ATAGAATCTC CCTCCCGACT CCCAAACTTC AGGTTGAGGA

1565  AAGCCAGTGC CAGAAGAGCC AAGGACAGGT ACGGCTGTCA TCACTTAGAC
      TTCGGTCACG GTCTTCTCGG TTCCTGTCCA TGCCGACAGT AGTGAATCTG

1615  CTCACCCTGT GGAGCCACAC CCTAGGGTTG GCCAATCTAC TCCCAGGAGC
      GAGTGGGACA CCTCGGTGTG GGATCCCAAC CGGTTAGATG AGGGTCCTCG

1665  AGGGAGGGCA GGAGCCAGGG CTGGGCATAA AAGTCAGGGC AGAGCCATCT
      TCCCTCCCGT CCTCGGTCCC GACCCGTATT TTCAGTCCCG TCTCGGTAGA
```

FIG.8A-4

```
1715  ATTGCTTACA TTTGCTTCTG ACACAACTGT GTTCACTAGC AACCTCAAAC
      TAACGAATGT AAACGAAGAC TGTGTTGACA CAAGTGATCG TTGGAGTTTG
-----------------------------------------------------------
1765  AGACAC
      TCTGTG
-----------------------------------------------------------
      BamHI
      ~~~~~
2191  GATCCTGAGA ACTTCAGGGT GAGTCTATGG GACCCTTGAT GTTTTCTTTC
      CTAGGACTCT TGAAGTCCCA CTCAGATACC CTGGGAACTA CAAAAGAAAG
-----------------------------------------------------------
2241  CCCTTCTTTT CTATGGTTAA GTTCATGTCA TAGGAAGGGG AGAAGTAACA
      GGGAAGAAAA GATACCAATT CAAGTACAGT ATCCTTCCCC TCTTCATTGT
-----------------------------------------------------------
2291  GGGTACAGTT TAGAATGGGA AACAGACGAA TGATTGCATC AGTGTGGAAG
      CCCATGTCAA ATCTTACCCT TTGTCTGCTT ACTAACGTAG TCACACCTTC
-----------------------------------------------------------
2341  TCTCAGGATC GTTTTAGTTT CTTTTATTTG CTGTTCATAA CAATTGTTTT
      AGAGTCCTAG CAAAATCAAA GAAAATAAAC GACAAGTATT GTTAACAAAA
-----------------------------------------------------------
2391  CTTTTGTTTA ATTCTTGCTT TCTTTTTTTT TCTTCTCCGC AATTTTTACT
      GAAAACAAAT TAAGAACGAA AGAAAAAAAA AGAAGAGGCG TTAAAAATGA
-----------------------------------------------------------
2441  ATTATACTTA ATGCCTTAAC ATTGTGTATA ACAAAAGGAA ATATCTCTGA
      TAATATGAAT TACGGAATTG TAACACATAT TGTTTTCCTT TATAGAGACT
```

FIG.8A—5

```
2491  GATACATTAA GTAACTTAAA AAAAAACTTT ACACAGTCTG CCTAGTACAT
      CTATGTAATT CATTGAATTT TTTTTTGAAA TGTGTCAGAC GGATCATGTA

2541  TACTATTTGG AATATATGTG TGCTTATTTG CATATTCATA ATCTCCCTAC
      ATGATAAACC TTATATACAC ACGAATAAAC GTATAAGTAT TAGAGGGATG

2591  TTTATTTTCT TTTATTTTTA ATTGATACAT AATCATTATA CATATTTATG
      AAATAAAAGA AAATAAAAAT TAACTATGTA TTAGTAATAT GTATAAATAC

2641  GGTTAAAGTG TAATGTTTTA ATATGTGTAC ACATATTGAC CAAATCAGGG
      CCAATTTCAC ATTACAAAAT TATACACATG TGTATAACTG GTTTAGTCCC

2691  TAATTTTGCA TTTGTAATTT TAAAAAATGC TTTCTTCTTT TAATATACTT
      ATTAAAACGT AAACATTAAA ATTTTTTACG AAAGAAGAAA ATTATATGAA

2741  TTTTGTTTAT CTTATTTCTA ATACTTTCCC TAATCTCTTT CTTTCAGGGC
      AAAACAAATA GAATAAAGAT TATGAAAGGG ATTAGAGAAA GAAAGTCCCG

2791  AATAATGATA CAATGTATCA TGCCTCTTTG CACCATTCTA AAGAATAACA
      TTATTACTAT GTTACATAGT ACGGAGAAAC GTGGTAAGAT TTCTTATTGT

2841  GTGATAATTT CTGGGTTAAG GCAATAGCAA TATTTCTGCA TATAAATATT
      CACTATTAAA GACCCAATTC CGTTATCGTT ATAAAGACGT ATATTTATAA

2891  TCTGCATATA AATTGTAACT CATGTAAGAG GTTTCATATT GCTAATAGCA
      AGACGTATAT TTAACATTGA CTACATTCTC CAAAGTATAA CGATTATCGT
```

FIG.8A-6

```
2941  GCTACAATCC AGCTACCATT CTGCTTTTAT TTTATGGTTG GGATAAGGCT
      CGATGTTAGG TCGATGGTAA GACGAAAATA AAATACCAAC CCTATTCCGA

2991  GGATTATTCT GAGTCCAAGC TAGGCCCTTT TGCTAATCAT GTTCATACCT
      CCTAATAAGA CTCAGGTTCG ATCCGGGAAA ACGATTAGTA CAAGTATGGA

3041  CTTATCTTCC TCCCACAGCT CCTGGGCAAC GTGCTGGTCT GTGTGCTGGC
      GAATAGAAGG AGGGTGTCGA GGACCCGTTG CACGACCAGA CACACGACCG

                     EcoRI
                    ~~~~~~~
3091  CCATCACTTT GGCAAAGAAT TCACCCCTGA GGTGCAGGCT TCCTGGCAGA
      GGTAGTGAAA CCGTTTCTTA AGTGGGGACT CCACGTCCGA AGGACCGTCT

3141  AGATGGTGAC TGCAGTGGCC AGTGCCCTGT CCTCCAGATA CCACTGAGCC
      TCTACCACTG ACGTCACCGG TCACGGGACA GGAGGTCTAT GGTGACTCGG

3191  TCTTGCCCAT GATTCAGAGC TTTCAAGGAT AGGCTTTATT CTGCAAGCAA
      AGAACGGGTA CTAAGTCTCG AAAGTTCCTA TCCGAAATAA GACGTTCGTT

3241  TACAAATAAT AAATCTATTC TGCTGAGAGA TCACACATGA TTTTCTTCAG
      ATGTTTATTA TTTAGATAAG ACGACTCTCT AGTGTGTACT AAAAGAAGTC

3291  CTCTTTTTTT TACATCTTTT TAAATATATG AGCCACAAAG GGTTTATATT
      GAGAAAAAAA ATGTAGAAAA ATTTATATAC TCGGTGTTTC CCAAATATAA
```

FIG.8A—7

```
3341  GAGGGAAGTG TGTATGTGTA TTTCTGCATG CCTGTTTGTG TTTGTGGTGT
      CTCCCTTCAC ACATACACAT AAAGACGTAC GGACAAACAC AAACACCACA

3391  GTGCATGCTC CTCATTTATT TTTATATGAG ATGTGCATTT TGATGAGCAA
      CACGTACGAG GAGTAAATAA AAATATACTC TACACGTAAA ACTACTCGTT

3441  ATAAAAGCAG TAAAGACACT TGTACACGGG AGTTCTGCAA GTGGGAGTAA
      TATTTTCGTC ATTTCTGTGA ACATGTGCCC TCAAGACGTT CACCCTCATT

3491  ATGGTGTTGG AGAAATCCGG TGGGAAGAAA GACCTCTATA GGACAGGACT
      TACCACAACC TCTTTAGGCC ACCCTTCTTT CTGGAGATAT CCTGTCCTGA

3541  TCTCAGAAAC AGATGTTTTG GAAGAGATGG GAAAAGGTTC AGTGAAGACC
      AGAGTCTTTG TCTACAAAAC CTTCTCTACC CTTTTCCAAG TCACTTCTGG

3591  TGGGGGCTGG ATTGATTGCA GCTGAGTAGC AAGGATGGTT CTTAATGAAG
      ACCCCCGACC TAACTAACGT CGACTCATCG TTCCTACCAA GAATTACTTC

                   NheI
                   ~~~~~~
3641  GGAAAGTGTT CCAGCTAGCG TGCTAGTCTC CCGGAACTAT CACTCTTTCA
      CCTTTCACAA GGTCGATCGC ACGATCAGAG GGCCTTGATA GTGAGAAAGT

3691  CAGTCTGCTT TGGAAGGACT GGGCTTAGTA TGAAAAGTTA GGACTGAGAA
      GTCAGACGAA ACCTTCCTGA CCCGAATCAT ACTTTTCAAT CCTGACTCTT
```

FIG.8A-8

```
3741  GAATTTGAAA GGGGGCTTTT TGTAGCTTGA TATTCACTAC TGTCTTATTA
      CTTAAACTTT CCCCCGAAAA ACATCGAACT ATAAGTGATG ACAGAATAAT

3791  CCCTATCATA GGCCCACCCC AAATGGAAGT CCCATTCTTC CTCAGGATGT
      GGGATAGTAT CCGGGTGGGG TTTACCTTCA GGGTAAGAAG GAGTCCTACA

3841  TTAAGATTAG CATTCAGGAA GAGATCAGAG GTCTGCTGGC TCCCTTATCA
      AATTCTAATC GTAAGTCCTT CTCTAGTCTC CAGACGACCG AGGGAATAGT

                            NheI  EcoRV
3891  TGTCCCTTAT GGTGCTTCTG GCTAGCGATA TCACCGGTAT
      ACAGGGAATA CCACGAAGAC CGATCGCTAT AGTGGCCATA
```

FIG.8A-9

| FIG.8B-1 |
|---|
| FIG.8B-2 |
| FIG.8B-3 |
| FIG.8B-4 |
| FIG.8B-5 |
| FIG.8B-6 |
| FIG.8B-7 |
| FIG.8B-8 |
| FIG.8B-9 |
| FIG.8B-10 |

SEQ ID NO.: 2
Full sequence ClaI-ClaI

```
      ClaI            XhoI
      ~~~~            ~~~~~~
 15   CGATGAAGCT TCCTCGAGGC AGAAGAGTCA AGCATTTGCC TAAGGTCGGA
      GCTACTTCGA AGGAGCTCCG TCTTCTCAGT TCGTAAACGG ATTCCAGCCT
-------------------------------------------------------------
 65   CATGTCAGAG GCAGTGCCAG ACCTATGTGA GACTCTGCAG CTACTGCTCA
      GTACAGTCTC CGTCACGGTC TGGATACACT CTGAGACGTC GATGACGAGT
-------------------------------------------------------------
115   TGGGCCCTGT GCTGCACTGA TGAGGAGGAT CAGATGGATG GGGCAATGAA
      ACCCGGGACA CGACGTGACT ACTCCTCCTA GTCTACCTAC CCCGTTACTT
-------------------------------------------------------------
165   GCAAAGGAAT CATTCTGTGG ATAAAGGAGA CAGCCATGAA GAAGTCTATG
      CGTTTCCTTA GTAAGACACC TATTTCCTCT GTCGGTACTT CTTCAGATAC
-------------------------------------------------------------
215   ACTGTAAATT TGGGAGCAGG AGTCTCTAAG GACTTGGATT TCAAGGAATT
      TGACATTTAA ACCCTCGTCC TCAGAGATTC CTGAACCTAA AGTTCCTTAA
-------------------------------------------------------------
265   TTGACTCAGC AAACACAAGA CCCTCACGGT GACTTTGCGA GCTGGTGTGC
      AACTGAGTCG TTTGTGTTCT GGGAGTGCCA CTGAAACGCT CGACCACACG
-------------------------------------------------------------
315   CAGATGTGTC TATCAGAGGT TCCAGGGAGG GTGGGGTGGG GTCAGGGCTG
      GTCTACACAG ATAGTCTCCA AGGTCCCTCC CACCCCACCC CAGTCCCGAC
-------------------------------------------------------------
```

```
365  GCCACCAGCT ATCAGGGCCC AGATGGGTTA TAGGCTGGCA GGCTCAGATA
     CGGTGGTCGA TAGTCCCGGG TCTACCCAAT ATCCGACCGT CCGAGTCTAT
-----------------------------------------------------------
415  GGTGGTTAGG TCAGGTTGGT GGTGCTGGGT GGAGTCCATG ACTCCCAGGA
     CCACCAATCC AGTCCAACCA CCACGACCCA CCTCAGGTAC TGAGGGTCCT
-----------------------------------------------------------
465  GCCAGGAGAG ATAGACCATG AGTAGAGGGC AGACATGGGA AAGGTGGGGG
     CGGTCCTCTC TATCTGGTAC TCATCTCCCG TCTGTACCCT TTCCACCCCC
-----------------------------------------------------------
515  AGGCACAGCA TAGCAGCATT TTTCATTCTA CTACTACATG GGACTGCTCC
     TCCGTGTCGT ATCGTCGTAA AAAGTAAGAT GATGATGTAC CCTGACGAGG
-----------------------------------------------------------
565  CCTATACCCC CAGCTAGGGG CAAGTGCCTT GACTCCTATG TTTTCAGGAT
     GGATATGGGG GTCGATCCCC GTTCACGGAA CTGAGGATAC AAAAGTCCTA
-----------------------------------------------------------
615  CATCATCTAT AAAGTAAGAG TAATAATTGT GTCTATCTCA TAGGGTTATT
     GTAGTAGATA TTTCATTCTC ATTATTAACA CAGATAGAGT ATCCCAATAA
-----------------------------------------------------------
665  ATGAGGATCA AAGGAGATGC ACACTCTCTG GACCAGTGGC CTAACAGTTC
     TACTCCTAGT TTCCTCTACG TGTGAGAGAC CTGGTCACCG GATTGTCAAG
-----------------------------------------------------------
715  ACGACAGAGC TATGGGCTTC CTATGTATGG GTCAGTGGTC TCAATGTAGC
     TGCTGTCTCG ATACCCGAAG GATACATACC CAGTCACCAG AGTTACATCG
-----------------------------------------------------------
765  AGGCAAGTTC CAGAAGATAG CATCAACCAC TGTTAGAGAT ATACTGCCAG
     TCCGTTCAAG GTCTTCTATC GTAGTTGGTG ACAATCTCTA TATGACGGTC
-----------------------------------------------------------
```

FIG.8B-2

```
815   TCTCAGAGCC TGATGTTAAT TTAGCAATGG GCTGGGACCC TCCTCCAGTA
      AGAGTCTCGG ACTACAATTA AATCGTTACC CGACCCTGGG AGGAGGTCAT
-----------------------------------------------------------
                    XhoI     SpeI    KpnI  SalI
                  ~~~~~~~~ ~~~~~~  ~~~~~~~~~~~~~
865   GAACCTTCTA ACCAGCCTCG AGGGACTAGT CGGTACCGTC GACAACCTCC
      CTTGGAAGAT TGGTCGGAGC TCCCTGATCA GCCATGGCAG CTGTTGGAGG
-----------------------------------------------------------
915   TATTTGACAC CACTGATTAC CCCATTGATA GTCACACTTT GGGTTGTAAG
      ATAAACTGTG GTGACTAATG GGGTAACTAT CAGTGTGAAA CCCAACATTC
-----------------------------------------------------------
965   TGACTTTTTA TTTATTTGTA TTTTTGACTG CATTAAGAGG TCTCTAGTTT
      ACTGAAAAAT AAATAAACAT AAAAACTGAC GTAATTCTCC AGAGATCAAA
-----------------------------------------------------------
1015  TTTATCTCTT GTTTCCCAAA ACCTAATAAG TAACTAATGC ACAGAGCACA
      AAATAGAGAA CAAAGGGTTT TGGATTATTC ATTGATTACG TGTCTCGTGT
-----------------------------------------------------------
1065  TTGATTTGTA TTTATTCTAT TTTTAGACAT AATTTATTAG CATGCATGAG
      AACTAAACAT AAATAAGATA AAAATCTGTA TTAAATAATC GTACGTACTC
-----------------------------------------------------------
1115  CAAATTAAGA AAAACAACAA CAAATGAATG CATATATATG TATATGTATG
      GTTTAATTCT TTTTGTTGTT GTTTACTTAC GTATATATAC ATATACATAC
-----------------------------------------------------------
1165  TGTGTATATA TACACATATA TATATATATT TTTTTTCTTT TCTTACCAGA
      ACACATATAT ATGTGTATAT ATATATATAA AAAAAAGAAA AGAATGGTCT
-----------------------------------------------------------
1215  AGGTTTTAAT CCAAATAAGG AGAAGATATG CTTAGAACTG AGGTAGAGTT
      TCCAAAATTA GGTTTATTCC TCTTCTATAC GAATCTTGAC TCCATCTCAA
-----------------------------------------------------------
```

FIG.8B–3

```
1265  TTCATCCATT CTGTCCTGTA AGTATTTTGC ATATTCTGGA GACGCAGGAA
      AAGTAGGTAA GACAGGACAT TCATAAAACG TATAAGACCT CTGCGTCCTT

1315  GAGATCCATC TACATATCCC AAAGCTGAAT TATGGTAGAC AAAGCTCTTC
      CTCTAGGTAG ATGTATAGGG TTTCGACTTA ATACCATCTG TTTCGAGAAG

1365  CACTTTTAGT GCATCAATTT CTTATTTGTG TAATAAGAAA ATTGGGAAAA
      GTGAAAATCA CGTAGTTAAA GAATAAACAC ATTATTCTTT TAACCCTTTT

                                                SnaBI
                                               ~~~~~~~
1415  CGATCTTCAA TATGCTTACC AAGCTGTGAT TCCAAATATT ACGTAAATAC
      GCTAGAAGTT ATACGAATGG TTCGACACTA AGGTTTATAA TGCATTTATG

1465  ACTTGCAAAG GAGGATGTTT TTAGTAGCAA TTTGTACTGA TGGTATGGGG
      TGAACGTTTC CTCCTACAAA AATCATCGTT AAACATGACT ACCATACCCC

1515  CCAAGAGATA TATCTTAGAG GGAGGGCTGA GGGTTTGAAG TCCAACTCCT
      GGTTCTCTAT ATAGAATCTC CCTCCCGACT CCCAAACTTC AGGTTGAGGA

1565  AAGCCAGTGC CAGAAGAGCC AAGGACAGGT ACGGCTGTCA TCACTTAGAC
      TTCGGTCACG GTCTTCTCGG TTCCTGTCCA TGCCGACAGT AGTGAATCTG

1615  CTCACCCTGT GGAGCCACAC CCTAGGGTTG GCCAATCTAC TCCCAGGAGC
      GAGTGGGACA CCTCGGTGTG GGATCCCAAC CGGTTAGATG AGGGTCCTCG

1665  AGGGAGGGCA GGAGCCAGGG CTGGGCATAA AAGTCAGGGC AGAGCCATCT
      TCCCTCCCGT CCTCGGTCCC GACCCGTATT TTCAGTCCCG TCTCGGTAGA
```

FIG.8B-4

```
1715  ATTGCTTACA TTTGCTTCTG ACACAACTGT GTTCACTAGC AACCTCAAAC
      TAACGAATGT AAACGAAGAC TGTGTTGACA CAAGTGATCG TTGGAGTTTG

              NcoI
              ~~~~~~~
1765  AGACACCATG GGTCATTTCA CAGAGGAGGA CAAGGCTACT ATCACAAGCC
      TCTGTGGTAC CCAGTAAAGT GTCTCCTCCT GTTCCGATGA TAGTGTTCGG

1815  TGTGGGGCAA GGTGAATGTG GAAGATGCTG GAGGAGAAAC CCTGGGAAGG
      ACACCCCGTT CCACTTACAC CTTCTACGAC CTCCTCTTTG GGACCCTTCC

1865  TAGGCTCTGG TGACCAGGAC AAGGGAGGGA AGGAAGGACC CTGTGCCTGG
      ATCCGAGACC ACTGGTCCTG TTCCCTCCCT TCCTTCCTGG GACACGGACC

1915  CAAAAGTCCA GGTCGCTTCT CAGGATTTGT GGCACCTTCT GACTGTCAAA
      GTTTTCAGGT CCAGCGAAGA GTCCTAAACA CCGTGGAAGA CTGACAGTTT

                                            NcoI
                                            ~~~~~~~
1965  CTGTTCTTGT CAATCTCACA GGCTCCTGGT TGTCTACCCA TGGACCCAGA
      GACAAGAACA GTTAGACTGT CCGAGGACCA ACAGATGGGT ACCTGGGTCT

2015  GGTTCTTTGA CAGCTTTGGC AACCTGTCCT CTGCCTCTGC CATCATGGGC
      CCAAGAAACT GTCGAAACCG TTGGACAGGA GACGGAGACG GTAGTACCCG

2065  AACCCCAAAG TCAAGGCACA TGGCAAGAAG GTGCTGACTT CCTTGGGAGA
      TTGGGGTTTC AGTTCCGTGT ACCGTTCTTC CACGACTGAA GGAACCCTCT
```

FIG.8B–5

```
2115  TGCCATAAAG CACCTGGATG ATCTCAAGGG CACCTTTGCC CAGCTGAGTG
      ACGGTATTTC GTGGACCTAC TAGAGTTCCC GTGGAAACGG GTCGACTCAC

                                BamHI
                               ~~~~~~~
2165  AACTGCACTG TGACAAGCTG CATGTGGATC CTGAGAACTT CAGGGTGAGT
      TTGACGTGAC ACTGTTCGAC GTACACCTAG GACTCTTGAA GTCCCACTCA

2215  CTATGGGACC CTTGATGTTT TCTTTCCCCT TCTTTTCTAT GGTTAAGTTC
      GATACCCTGG GAACTACAAA AGAAAGGGGA AGAAAAGATA CCAATTCAAG

2265  ATGTCATAGG AAGGGGAGAA GTAACAGGGT ACAGTTTAGA ATGGGAAACA
      TACAGTATCC TTCCCCTCTT CATTGTCCCA TGTCAAATCT TACCCTTTGT

2315  GACGAATGAT TGCATCAGTG TGGAAGTCTC AGGATCGTTT TAGTTTCTTT
      CTGCTTACTA ACGTAGTCAC ACCTTCAGAG TCCTAGCAAA ATCAAAGAAA

2365  TATTTGCTGT TCATAACAAT TGTTTTCTTT TGTTTAATTC TTGCTTTCTT
      ATAAACGACA AGTATTGTTA ACAAAAGAAA ACAAATTAAG AACGAAAGAA

2415  TTTTTTTCTT CTCCGCAATT TTTACTATTA TACTTAATGC CTTAACATTG
      AAAAAAAGAA GAGGCGTTAA AAATGATAAT ATGAATTACG GAATTGTAAC

2465  TGTATAACAA AAGGAAATAT CTCTGAGATA CATTAAGTAA CTTAAAAAAA
      ACATATTGTT TTCCTTTATA GAGACTCTAT GTAATTCATT GAATTTTTTT
```

FIG.8B-6

```
2515  AACTTTACAC AGTCTGCCTA GTACATTACT ATTTGGAATA TATGTGTGCT
      TTGAAATGTG TCAGACGGAT CATGTAATGA TAAACCTTAT ATACACACGA
-----------------------------------------------------------
2565  TATTTGCATA TTCATAATCT CCCTACTTTA TTTTCTTTTA TTTTTAATTG
      ATAAACGTAT AAGTATTAGA GGGATGAAAT AAAAGAAAAT AAAAATTAAC
-----------------------------------------------------------
2615  ATACATAATC ATTATACATA TTTATGGGTT AAAGTGTAAT GTTTTAATAT
      TATGTATTAG TAATATGTAT AAATACCCAA TTTCACATTA CAAAATTATA
-----------------------------------------------------------
2665  GTGTACACAT ATTGACCAAA TCAGGGTAAT TTTGCATTTG TAATTTTAAA
      CACATGTGTA TAACTGGTTT AGTCCCATTA AAACGTAAAC ATTAAAATTT
-----------------------------------------------------------
2715  AAATGCTTTC TTCTTTTAAT ATACTTTTTT GTTTATCTTA TTTCTAATAC
      TTTACGAAAG AAGAAAATTA TATGAAAAAA CAAATAGAAT AAAGATTATG
-----------------------------------------------------------
2765  TTTCCCTAAT CTCTTTCTTT CAGGGCAATA ATGATACAAT GTATCATGCC
      AAAGGGATTA GAGAAAGAAA GTCCCGTTAT TACTATGTTA CATAGTACGG
-----------------------------------------------------------
2815  TCTTTGCACC ATTCTAAAGA ATAACAGTGA TAATTTCTGG GTTAAGGCAA
      AGAAACGTGG TAAGATTTCT TATTGTCACT ATTAAAGACC CAATTCCGTT
-----------------------------------------------------------
2865  TAGCAATATT TCTGCATATA AATATTTCTG CATATAAATT GTAACTGATG
      ATCGTTATAA AGACGTATAT TTATAAAGAC GTATATTTAA CATTGACTAC
-----------------------------------------------------------
2915  TAAGAGGTTT CATATTGCTA ATAGCAGCTA CAATCCAGCT ACCATTCTGC
      ATTCTCCAAA GTATAACGAT TATCGTCGAT GTTAGGTCGA TGGTAAGACG
-----------------------------------------------------------
```

FIG.8B-7

```
2965  TTTTATTTTA TGGTTGGGAT AAGGCTGGAT TATTCTGAGT CCAAGCTAGG
      AAAATAAAAT ACCAACCCTA TTCCGACCTA ATAAGACTCA GGTTCGATCC
-----------------------------------------------------------
3015  CCCTTTTGCT AATCATGTTC ATACCTCTTA TCTTCCTCCC ACAGCTCCTG
      GGGAAAACGA TTAGTACAAG TATGGAGAAT AGAAGGAGGG TGTCGAGGAC
-----------------------------------------------------------
                                                EcoRI
                                                ~~~~~~
3065  GGCAACGTGC TGGTCTGTGT GCTGGCCCAT CACTTTGGCA AAGAATTCAC
      CCGTTGCACG ACCAGACACA CGACCGGGTA GTGAAACCGT TTCTTAAGTG
-----------------------------------------------------------
3115  CCCTGAGGTG CAGGCTTCCT GGCAGAAGAT GGTGACTGCA GTGGCCAGTG
      GGGACTCCAC GTCCGAAGGA CCGTCTTCTA CCACTGACGT CACCGGTCAC
-----------------------------------------------------------
3165  CCCTGTCCTC CAGATACCAC TGAGCCTCTT GCCCATGATT CAGAGCTTTC
      GGGACAGGAG GTCTATGGTG ACTCGGAGAA CGGGTACTAA GTCTCGAAAG
-----------------------------------------------------------
3215  AAGGATAGGC TTTATTCTGC AAGCAATACA AATAATAAAT CTATTCTGCT
      TTCCTATCCG AAATAAGACG TTCGTTATGT TTATTATTTA GATAAGACGA
-----------------------------------------------------------
3265  GAGAGATCAC ACATGATTTT CTTCAGCTCT TTTTTTTACA TCTTTTTAAA
      CTCTCTAGTG TGTACTAAAA GAAGTCGAGA AAAAAAATGT AGAAAAATTT
-----------------------------------------------------------
3315  TATATGAGCC ACAAAGGGTT TATATTGAGC GAAGTGTGTA TGTGTATTTC
      ATATACTCGG TGTTTCCCAA ATATAACTCC CTTCACACAT ACACATAAAG
-----------------------------------------------------------
```

FIG.8B-8

```
3365  TGCATGCCTG TTTGTGTTTG TGGTGTGTGC ATGCTCCTCA TTTATTTTTA
      ACGTACGGAC AAACACAAAC ACCACACACG TACGAGGAGT AAATAAAAAT
--------------------------------------------------------------
3415  TATGAGATGT GCATTTTGAT GAGCAAATAA AAGCAGTAAA GACACTTGTA
      ATACTCTACA CGTAAAACTA CTCGTTTATT TTCGTCATTT CTGTGAACAT
--------------------------------------------------------------
3465  CACGGGAGTT CTGCAAGTGG GAGTAAATGG TGTTGGAGAA ATCCGGTGGG
      GTGCCCTCAA GACGTTCACC CTCATTTACC ACAACCTCTT TAGGCCACCC
--------------------------------------------------------------
3515  AAGAAAGACC TCTATAGGAC AGGACTTCTC AGAAACAGAT GTTTTGGAAG
      TTCTTTCTGG AGATATCCTG TCCTGAAGAG TCTTTGTCTA CAAAACCTTC
--------------------------------------------------------------
3565  AGATGGGAAA AGGTTCAGTG AAGACCTGGG GGCTGGATTG ATTGCAGCTG
      TCTACCCTTT TCCAAGTCAC TTCTGGACCC CCGACCTAAC TAACGTCGAC
--------------------------------------------------------------
                                               NheI
                                              -------
3615  AGTAGCAAGG ATGGTTCTTA ATGAAGGGAA AGTGTTCCAG CTAGCGTGCT
      TCATCGTTCC TACCAAGAAT TACTTCCCTT TCACAAGGTC GATCGCACGA
--------------------------------------------------------------
3665  AGTCTCCCGG AACTATCACT CTTTCACAGT CTGCTTTGGA AGGACTGGGC
      TCAGAGGGCC TTGATAGTGA GAAAGTGTCA GACGAAACCT TCCTGACCCG
--------------------------------------------------------------
3715  TTAGTATGAA AAGTTAGGAC TGAGAAGAAT TTGAAAGGGG GCTTTTTGTA
      AATCATACTT TTCAATCCTG ACTCTTCTTA AACTTTCCCC CGAAAAACAT
--------------------------------------------------------------
```

FIG.8B-9

```
3765  GCTTGATATT CACTACTGTC TTATTACCCT ATCATAGGCC CACCCCAAAT
      CGAACTATAA GTGATGACAG AATAATGGGA TAGTATCCGG GTGGGGTTTA

3815  GGAAGTCCCA TTCTTCCTCA GGATGTTTAA GATTAGCATT CAGGAAGAGA
      CCTTCAGGGT AAGAAGGAGT CCTACAAATT CTAATCGTAA GTCCTTCTCT

                                                     NheI
                                                     ~~~~
3865  TCAGAGGTCT GCTGGCTCCC TTATCATGTC CCTTATGGTG CTTCTGGCTA
      AGTCTCCAGA CGACCGAGGG AATAGTACAG GGAATACCAC GAAGACCGAT

      NheI
      ~~
        EcoRV
       ~~~~~~
3915  GCGATATCAC CGGTAT
      CGCTATAGTG GCCATA
```

FIG.8B-10

| FIG.9A-1 |
|---|
| FIG.9A-2 |
| FIG.9A-3 |
| FIG.9A-4 |
| FIG.9A-5 |
| FIG.9A-6 |
| FIG.9A-7 |
| FIG.9A-8 |

SEQ ID NO.: 3
Without Aγ-globin coding sequence

```
     ClaI          XhoI
     ~~~~          ~~~~~~
10   CGATGAAGCT TCCTCGAGGC AGAAGAGTCA AGCATTTGCC TAAGGTCGGA
     GCTACTTCGA AGGAGCTCCG TCTTCTCAGT TCGTAAACGG ATTCCAGCCT
---------------------------------------------------------
60   CATGTCAGAG GCAGTGCCAG ACCTATGTGA GACTCTGCAG CTACTGCTCA
     GTACAGTCTC CGTCACGGTC TGGATACACT CTGAGACGTC GATGACGAGT
---------------------------------------------------------
110  TGGGCCCTGT GCTGCACTGA TGAGGAGGAT CAGATGGATG GGGCAATGAA
     ACCCGGGACA CGACGTGACT ACTCCTCCTA GTCTACCTAC CCCGTTACTT
---------------------------------------------------------
160  GCAAAGGAAT CATTCTGTGG ATAAAGGAGA CAGCCATGAA GAAGTCTATG
     CGTTTCCTTA GTAAGACACC TATTTCCTCT GTCGGTACTT CTTCAGATAC
---------------------------------------------------------
210  ACTGTAAATT TGGGAGCAGG AGTCTCTAAG GACTTGGATT TCAAGGAATT
     TGACATTTAA ACCCTCGTCC TCAGAGATTC CTGAACCTAA AGTTCCTTAA
---------------------------------------------------------
260  TTGACTCAGC AAACACAAGA CCCTCACGGT GACTTTGCGA GCTGGTGTGC
     AACTGAGTCG TTTGTGTTCT GGGAGTGCCA CTGAAACGCT CGACCACACG
---------------------------------------------------------
310  CAGATGTGTC TATCAGAGGT TCCAGGGAGG GTGGGGTGGG GTCAGGGCTG
     GTCTACACAG ATAGTCTCCA AGGTCCCTCC CACCCCACCC CAGTCCCGAC
---------------------------------------------------------
```

```
360  GCCACCAGCT ATCAGGGCCC AGATGGGTTA TAGGCTGGCA GGCTCAGATA
     CGGTGGTCGA TAGTCCCGGG TCTACCCAAT ATCCGACCGT CCGAGTCTAT
-------------------------------------------------------------
410  GGTGGTTAGG TCAGGTTGGT GGTGCTGGGT GGAGTCCATG ACTCCCAGGA
     CCACCAATCC AGTCCAACCA CCACGACCCA CCTCAGGTAC TGAGGGTCCT
-------------------------------------------------------------
460  GCCAGGAGAG ATAGACCATG AGTAGAGGGC AGACATGGGA AAGGTGGGGG
     CGGTCCTCTC TATCTGGTAC TCATCTCCCG TCTGTACCCT TTCCACCCCC
-------------------------------------------------------------
510  AGGCACAGCA TAGCAGCATT TTTCATTCTA CTACTACATG GGACTGCTCC
     TCCGTGTCGT ATCGTCGTAA AAAGTAAGAT GATGATGTAC CCTGACGAGG
-------------------------------------------------------------
560  CCTATACCCC CAGCTAGGGG CAAGTGCCTT GACTCCTATG TTTTCAGGAT
     GGATATGGGG GTCGATCCCC GTTCACGGAA CTGAGGATAC AAAAGTCCTA
-------------------------------------------------------------
610  CATCATCTAT AAAGTAAGAG TAATAATTGT GTCTATCTCA TAGGGTTATT
     GTAGTAGATA TTTCATTCTC ATTATTAACA CAGATAGAGT ATCCCAATAA
-------------------------------------------------------------
660  ATGAGGATCA AAGGAGATGC ACACTCTCTG GACCAGTGGC CTAACAGTTC
     TACTCCTAGT TTCCTCTACG TGTGAGAGAC CTGGTCACCG GATTGTCAAG
-------------------------------------------------------------
710  AGGACAGAGC TATGGGCTTC CTATGTATGG GTCAGTGGTC TCAATGTAGC
     TCCTGTCTCG ATACCCGAAG GATACATACC CAGTCACCAG AGTTACATCG
-------------------------------------------------------------
760  AGGCAAGTTC CAGAAGATAG CATCAACCAC TGTTAGAGAT ATACTGCCAG
     TCCGTTCAAG GTCTTCTATC GTAGTTGGTG ACAATCTCTA TATGACGGTC
-------------------------------------------------------------
810  TCTCAGAGCC TGATGTTAAT TTAGCAATGG GCTGGGACCC TCCTCCAGTA
     AGAGTCTCGG ACTACAATTA AATCGTTACC CGACCCTGGG AGGAGGTCAT
```

FIG.9A-2

```
                          XhoI       SpeI      KpnI
                        --------   -------   -------
860   GAACCTTCTA ACCAGCCTCG AGGGACTAGT CGGTACCGAT TTATTTCAAA
      CTTGGAAGAT TGGTCGGAGC TCCCTGATCA GCCATGGCTA AATAAAGTTT
---------------------------------------------------------------
910   TAGGTACGGA TAAGTAGATA TTGAGGTAAG CATTAGGTCT TATATTATGT
      ATCCATGCCT ATTCATCTAT AACTCCATTC GTAATCCAGA ATATAATACA
---------------------------------------------------------------
960   AACACTAATC TATTACTGCG CTGAAACTGT GGTCTTTATG AAAATTGTTT
      TTGTGATTAG ATAATGACGC GACTTTGACA CCAGAAATAC TTTTAACAAA
---------------------------------------------------------------
1010  TCACTACACT ATTGAGAAAT TAAGAGATAA TGGCAAAAGT CACAAAGAGT
      AGTGATGTGA TAACTCTTTA ATTCTCTATT ACCGTTTTCA GTGTTTCTCA
---------------------------------------------------------------
1060  ATATTCAAAA AGAAGTATAG CACTTTTTCC TTAGAAACCA CTGCTAACTG
      TATAAGTTTT TCTTCATATC GTGAAAAAGG AATCTTTGGT GACGATTGAC
---------------------------------------------------------------
1110  AAAGAGACTA AGATTTGTCC CGTCAAAAAT CCTGGACCTA TGCCTAAAAC
      TTTCTCTGAT TCTAAACAGG GCAGTTTTTA GGACCTGGAT ACGGATTTTG
---------------------------------------------------------------
1160  ACATTTCACA ATCCCTGAAC TTTTCAAAAA TTGGTACATG CTTTAGCTTT
      TGTAAAGTGT TAGGGACTTG AAAAGTTTTT AACCATGTAC GAAATCGAAA
---------------------------------------------------------------
1210  AAACTACAGG CCTCACTGGA GCTACAGACA AGAAGGTAAA AAACGGCTGA
      TTTGATGTCC GGAGTGACCT CGATGTCTGT TCTTCCATTT TTTGCCGACT
---------------------------------------------------------------
1260  CAAAAGAAGT CCTGGTATCC TCTATGATGG GAGAAGGAAA CTAGCTAAAG
      GTTTTCTTCA GGACCATAGG AGATACTACC CTCTTCCTTT GATCGATTTC
---------------------------------------------------------------
```

FIG.9A–3

```
1310  GGAAGAATAA ATTAGAGAAA AACTGGAATG ACTGAATCGG AACAAGGCAA
      CCTTCTTATT TAATCTCTTT TTGACCTTAC TGACTTAGCC TTGTTCCGTT
------------------------------------------------------------
1360  AGGCTATAAA AAAAATTAAG CAGCAGTATC CTCTTGGGGG CCCCTTCCCC
      TCCGATATTT TTTTTAATTC GTCGTCATAG GAGAACCCCC GGGGAAGGGG
------------------------------------------------------------
1410  ACACTATCTC AATGCAAATA TCTGTCTGAA ACGGTCCCTG GCTAAACTCC
      TGTGATAGAG TTACGTTTAT AGACAGACTT TGCCAGGGAC CGATTTGAGG
------------------------------------------------------------
         NcoI
        ------
1460  ACCCATGGGT TGGCCAGCCT TGCCTTGACC AATAGCCTTG ACAAGGCAAA
      TGGGTACCCA ACCGGTCGGA ACGGAACTGG TTATCGGAAC TGTTCCGTTT
------------------------------------------------------------
1510  CTTGACCAAT AGTCTTAGAG TATCCAGTGA GGCCAGGGGC CGGCGGCTGG
      GAACTGGTTA TCAGAATCTC ATAGGTCACT CCGGTCCCCG GCCGCCGACC
------------------------------------------------------------
1560  CTAGGGATGA AGAATAAAAG GAAGCACCCT TCAGCAGTTC CACACACTCG
      GATCCCTACT TCTTATTTTC CTTCGTGGGA AGTCGTCAAG GTGTGTGAGC
------------------------------------------------------------
1610  CTTCTGGAAC GTCTGAGATT ATCAATAAGC TCCTAGTCCA GACGC
      GAAGACCTTG CAGACTCTAA TAGTTATTCG AGGATCAGGT CTGCG
------------------------------------------------------------
      BamHI
      -----
2075  GATCCTGAGA ACTTCAGGGT GAGTCTATGG GACCCTTGAT GTTTTCTTTC
      CTAGGACTCT TGAAGTCCCA CTCAGATACC CTGGGAACTA CAAAAGAAAG
------------------------------------------------------------
```

FIG.9A-4

```
2125  CCCTTCTTTT CTATGGTTAA GTTCATGTCA TAGGAAGGGG AGAAGTAACA
      GGGAAGAAAA GATACCAATT CAAGTACAGT ATCCTTCCCC TCTTCATTGT
--------------------------------------------------------------
2175  GGGTACAGTT TAGAATGGGA AACAGACGAA TGATTGCATC AGTGTGGAAG
      CCCATGTCAA ATCTTACCCT TTGTCTGCTT ACTAACGTAG TCACACCTTC
--------------------------------------------------------------
2225  TCTCAGGATC GTTTTAGTTT CTTTTATTTG CTGTTCATAA CAATTGTTTT
      AGAGTCCTAG CAAAATCAAA GAAAATAAAC GACAAGTATT GTTAACAAAA
--------------------------------------------------------------
2275  CTTTTGTTTA ATTCTTGCTT TCTTTTTTTT TCTTCTCCGC AATTTTTACT
      GAAAACAAAT TAAGAACGAA AGAAAAAAAA AGAAGAGGCG TTAAAAATGA
--------------------------------------------------------------
2325  ATTATACTTA ATGCCTTAAC ATTGTGTATA ACAAAAGGAA ATATCTCTGA
      TAATATGAAT TACGGAATTG TAACACATAT TGTTTTCCTT TATAGAGACT
--------------------------------------------------------------
2375  GATACATTAA GTAACTTAAA AAAAAACTTT ACACAGTCTG CCTAGTACAT
      CTATGTAATT CATTGAATTT TTTTTTGAAA TGTGTCAGAC GGATCATGTA
--------------------------------------------------------------
2425  TACTATTTGG AATATATGTG TGCTTATTTG CATATTCATA ATCTCCCTAC
      ATGATAAACC TTATATACAC ACGAATAAAC GTATAAGTAT TAGAGGGATG
--------------------------------------------------------------
2475  TTTATTTTCT TTTATTTTTA ATTGATACAT AATCATTATA CATATTTATG
      AAATAAAAGA AAATAAAAAT TAACTATGTA TTAGTAATAT GTATAAATAC
--------------------------------------------------------------
2525  GGTTAAAGTG TAATGTTTTA ATATGTGTAC ACATATTGAC CAAATCAGGG
      CCAATTTCAC ATTACAAAAT TATACACATG TGTATAACTG GTTTAGTCCC
--------------------------------------------------------------
```

FIG.9A—5

```
2575  TAATTTTGCA TTTGTAATTT TAAAAAATGC TTTCTTCTTT TAATATACTT
      ATTAAAACGT AAACATTAAA ATTTTTTACG AAAGAAGAAA ATTATATGAA

2625  TTTTGTTTAT CTTATTTCTA ATACTTTCCC TAATCTCTTT CTTTCAGGGC
      AAAACAAATA GAATAAAGAT TATGAAAGGG ATTAGAGAAA GAAAGTCCCG

2675  AATAATGATA CAATGTATCA TGCCTCTTTG CACCATTCTA AAGAATAACA
      TTATTACTAT GTTACATAGT ACGGAGAAAC GTGGTAAGAT TTCTTATTGT

2725  GTGATAATTT CTGGGTTAAG GCAATAGCAA TATTTCTGCA TATAAATATT
      CACTATTAAA GACCCAATTC CGTTATCGTT ATAAAGACGT ATATTTATAA

2775  TCTGCATATA AATTGTAACT GATGTAAGAG GTTTCATATT GCTAATAGCA
      AGACGTATAT TTAACATTGA CTACATTCTC CAAAGTATAA CGATTATCGT

2825  GCTACAATCC AGCTACCATT CTGCTTTTAT TTTATGGTTG GGATAAGGCT
      CGATGTTAGG TCGATGGTAA GACGAAAATA AAATACCAAC CCTATTCCGA

2875  GGATTATTCT GAGTCCAAGC TAGGCCCTTT TGCTAATCAT GTTCATACCT
      CCTAATAAGA CTCAGGTTCG ATCCGGGAAA ACGATTAGTA CAAGTATGGA

2925  CTTATCTTCC TCCCACAGCT CCTGGGCAAC GTGCTGGTCT GTGTGCTGGC
      GAATAGAAGG AGGGTGTCGA GGACCCGTTG CACGACCAGA CACACGACCG

                           EcoRI
                          ~~~~~~~
2975  CCATCACTTT GGCAAAGAAT TCACCCCTGA GGTGCAGGCT TCCTGGCAGA
      GGTAGTGAAA CCGTTTCTTA AGTGGGGACT CCACGTCCGA AGGACCGTCT
```

FIG.9A-6

```
3025  AGATGGTGAC TGCAGTGGCC AGTGCCCTGT CCTCCAGATA CCACTGAGCC
      TCTACCACTG ACGTCACCGG TCACGGGACA GGAGGTCTAT GGTGACTCGG

3075  TCTTGCCCAT GATTCAGAGC TTTCAAGGAT AGGCTTTATT CTGCAAGCAA
      AGAACGGGTA CTAAGTCTCG AAAGTTCCTA TCCGAAATAA GACGTTCGTT

3125  TACAAATAAT AAATCTATTC TGCTGAGAGA TCACACATGA TTTTCTTCAG
      ATGTTTATTA TTTAGATAAG ACGACTCTCT AGTGTGTACT AAAAGAAGTC

3175  CTCTTTTTTT TACATCTTTT TAAATATATG AGCCACAAAG GGTTTATATT
      GAGAAAAAAA ATGTAGAAAA ATTTATATAC TCGGTGTTTC CCAAATATAA

3225  GAGGGAAGTG TGTATGTGTA TTTCTGCATG CCTGTTTGTG TTTGTGGTGT
      CTCCCTTCAC ACATACACAT AAAGACGTAC GGACAAACAC AAACACCACA

3275  GTGCATGCTC CTCATTTATT TTTATATGAG ATGTGCATTT TGATGAGCAA
      CACGTACGAG GAGTAAATAA AAATATACTC TACACGTAAA ACTACTCGTT

3325  ATAAAAGCAG TAAAGACACT TGTACACGGG AGTTCTGCAA GTGGGAGTAA
      TATTTTCGTC ATTTCTGTGA ACATGTGCCC TCAAGACGTT CACCCTCATT

3375  ATGGTGTTGG AGAAATCCGG TGGGAAGAAA GACCTCTATA GGACAGGACT
      TACCACAACC TCTTTAGGCC ACCCTTCTTT CTGGAGATAT CCTGTCCTGA

3425  TCTCAGAAAC AGATGTTTTG GAAGAGATGG GAAAAGGTTC AGTGAAGACC
      AGAGTCTTTG TCTACAAAAC CTTCTCTACC CTTTTCCAAG TCACTTCTGG
```

FIG.9A-7

```
3475  TGGGGGCTGG ATTGATTGCA GCTGAGTAGC AAGGATGGTT CTTAATGAAG
      ACCCCCGACC TAACTAACGT CGACTCATCG TTCCTACCAA GAATTACTTC
---------------------------------------------------------
                    NheI
                    ~~~~~~
3525  GGAAAGTGTT CCAGCTAGCG TGCTAGTCTC CCGGAACTAT CACTCTTTCA
      CCTTTCACAA GGTCGATCGC ACGATCAGAG GGCCTTGATA GTGAGAAAGT
---------------------------------------------------------
3575  CAGTCTGCTT TGGAAGGACT GGGCTTAGTA TGAAAAGTTA GGACTGAGAA
      GTCAGACGAA ACCTTCCTGA CCCGAATCAT ACTTTTCAAT CCTGACTCTT
---------------------------------------------------------
3625  GAATTTGAAA GGGGGCTTTT TGTAGCTTGA TATTCACTAC TGTCTTATTA
      CTTAAACTTT CCCCCGAAAA ACATCGAACT ATAAGTGATG ACAGAATAAT
---------------------------------------------------------
3675  CCCTATCATA GGCCCACCCC AAATGGAAGT CCCATTCTTC CTCAGGATGT
      GGGATAGTAT CCGGGTGGGG TTTACCTTCA GGGTAAGAAG GAGTCCTACA
---------------------------------------------------------
3725  TTAAGATTAG CATTCAGGAA GAGATCAGAG GTCTGCTGGC TCCCTTATCA
      AATTCTAATC GTAAGTCCTT CTCTAGTCTC CAGACGACCG AGGGAATAGT
---------------------------------------------------------
                             NheI  EcoRV
                             ~~~~~~~~~~~~
3775  TGTCCCTTAT GGTGCTTCTG GCTAGCGATA TCACCGGTAT
      ACAGGGAATA CCACGAAGAC CGATCGCTAT AGTGGCCATA
---------------------------------------------------------
```

FIG.9A–8

| FIG.9B-1 |
| --- |
| FIG.9B-2 |
| FIG.9B-3 |
| FIG.9B-4 |
| FIG.9B-5 |
| FIG.9B-6 |
| FIG.9B-7 |
| FIG.9B-8 |
| FIG.9B-9 |

SEQ ID NO.: 4
Full sequence ClaI-ClaI

```
     ClaI          XhoI
     ~~~~          ~~~~~~
 10  CGATGAAGCT TCCTCGAGGC AGAAGAGTCA AGCATTTGCC TAAGGTCGGA
     GCTACTTCGA AGGAGCTCCG TCTTCTCAGT TCGTAAACGG ATTCCAGCCT
---------------------------------------------------------
 60  CATGTCAGAG GCAGTGCCAG ACCTATGTGA GACTCTGCAG CTACTGCTCA
     GTACAGTCTC CGTCACGGTC TGGATACACT CTGAGACGTC GATGACGAGT
---------------------------------------------------------
110  TGGGCCCTGT GCTGCACTGA TGAGGAGGAT CAGATGGATG GGGCAATGAA
     ACCCGGGACA CGACGTGACT ACTCCTCCTA GTCTACCTAC CCCGTTACTT
---------------------------------------------------------
160  GCAAAGGAAT CATTCTGTGG ATAAAGGAGA CAGCCATGAA GAAGTCTATG
     CGTTTCCTTA GTAAGACACC TATTTCCTCT GTCGGTACTT CTTCAGATAC
---------------------------------------------------------
210  ACTGTAAATT TGGGAGCAGG AGTCTCTAAG GACTTGGATT TCAAGGAATT
     TGACATTTAA ACCCTCGTCC TCAGAGATTC CTGAACCTAA AGTTCCTTAA
---------------------------------------------------------
260  TTGACTCAGC AAACACAAGA CCCTCACGGT GACTTTGCGA GCTGGTGTGC
     AACTGAGTCG TTTGTGTTCT GGGAGTGCCA CTGAAACGCT CGACCACACG
---------------------------------------------------------
310  CAGATGTGTC TATCAGAGGT TCCAGGGAGG GTGGGGTGGG GTCAGGGCTG
     GTCTACACAG ATAGTCTCCA AGGTCCCTCC CACCCCACCC CAGTCCCGAC
---------------------------------------------------------
360  GCCACCAGCT ATCAGGGCCC AGATGGGTTA TAGGCTGGCA GGCTCAGATA
     CGGTGGTCGA TAGTCCCGGG TCTACCCAAT ATCCGACCGT CCGAGTCTAT
---------------------------------------------------------
```

```
410  GGTGGTTAGG TCAGGTTGGT GGTGCTGGGT GGAGTCCATG ACTCCCAGGA
     CCACCAATCC AGTCCAACCA CCACGACCCA CCTCAGGTAC TGAGGGTCCT
-------------------------------------------------------------
460  GCCAGGAGAG ATAGACCATG AGTAGAGGGC AGACATGGGA AAGGTGGGGG
     CGGTCCTCTC TATCTGGTAC TCATCTCCCG TCTGTACCCT TTCCACCCCC
-------------------------------------------------------------
510  AGGCACAGCA TAGCAGCATT TTTCATTCTA CTACTACATG GGACTGCTCC
     TCCGTGTCGT ATCGTCGTAA AAAGTAAGAT GATGATGTAC CCTGACGAGG
-------------------------------------------------------------
560  CCTATACCCC CAGCTAGGGG CAAGTGCCTT GACTCCTATG TTTTCAGGAT
     GGATATGGGG GTCGATCCCC GTTCACGGAA CTGAGGATAC AAAAGTCCTA
-------------------------------------------------------------
610  CATCATCTAT AAAGTAAGAG TAATAATTGT GTCTATCTCA TAGGGTTATT
     GTAGTAGATA TTTCATTCTC ATTATTAACA CAGATAGAGT ATCCCAATAA
-------------------------------------------------------------
660  ATGAGGATCA AAGGAGATGC ACACTCTCTG GACCAGTGGC CTAACAGTTC
     TACTCCTAGT TTCCTCTACG TGTGAGAGAC CTGGTCACCG GATTGTCAAG
-------------------------------------------------------------
710  AGGACAGAGC TATGGGCTTC CTATGTATGG GTCAGTGGTC TCAATGTAGC
     TCCTGTCTCG ATACCCGAAG GATACATACC CAGTCACCAG AGTTACATCG
-------------------------------------------------------------
760  AGGCAAGTTC CAGAAGATAG CATCAACCAC TGTTAGAGAT ATACTGCCAG
     TCCGTTCAAG GTCTTCTATC GTAGTTGGTG ACAATCTCTA TATGACGGTC
-------------------------------------------------------------
810  TCTCAGAGCC TGATGTTAAT TTAGCAATGG GCTGGGACCC TCCTCCAGTA
     AGAGTCTCGG ACTACAATTA AATCGTTACC CGACCCTGGG AGGAGGTCAT
```

FIG.9B-2

```
                            XhoI      SpeI     KpnI
                          ~~~~~~~   ~~~~~~   ~~~~~~
 860  GAACCTTCTA ACCAGCCTCG AGGGACTAGT CGGTACCGAT TTATTTCAAA
      CTTGGAAGAT TGGTCGGAGC TCCCTGATCA GCCATGGCTA AATAAAGTTT
----------------------------------------------------------
 910  TAGGTACGGA TAAGTAGATA TTGAGGTAAG CATTAGGTCT TATATTATGT
      ATCCATGCCT ATTCATCTAT AACTCCATTC GTAATCCAGA ATATAATACA
----------------------------------------------------------
 960  AACACTAATC TATTACTGCG CTGAAACTGT GGTCTTTATG AAAATTGTTT
      TTGTGATTAG ATAATGACGC GACTTTGACA CCAGAAATAC TTTTAACAAA
----------------------------------------------------------
1010  TCACTACACT ATTGAGAAAT TAAGAGATAA TGGCAAAAGT CACAAAGAGT
      AGTGATGTGA TAACTCTTTA ATTCTCTATT ACCGTTTTCA GTGTTTCTCA
----------------------------------------------------------
1060  ATATTCAAAA AGAAGTATAG CACTTTTTCC TTAGAAACCA CTGCTAACTG
      TATAAGTTTT TCTTCATATC GTGAAAAAGG AATCTTTGGT GACGATTGAC
----------------------------------------------------------
1110  AAAGAGACTA AGATTTGTCC CGTCAAAAAT CCTGGACCTA TGCCTAAAAC
      TTTCTCTGAT TCTAAACAGG GCAGTTTTTA GGACCTGGAT ACGGATTTTG
----------------------------------------------------------
1160  ACATTTCACA ATCCCTGAAC TTTTCAAAAA TTGGTACATG CTTTAGCTTT
      TGTAAAGTGT TAGGGACTTG AAAAGTTTTT AACCATGTAC GAAATCGAAA
----------------------------------------------------------
1210  AAACTACAGG CCTCACTGGA GCTACAGACA AGAAGGTAAA AAACGGCTGA
      TTTGATGTCC GGAGTGACCT CGATGTCTGT TCTTCCATTT TTTGCCGACT
----------------------------------------------------------
1260  CAAAAGAAGT CCTGGTATCC TCTATGATGG GAGAAGGAAA CTAGCTAAAG
      GTTTTCTTCA GGACCATAGG AGATACTACC CTCTTCCTTT GATCGATTTC
----------------------------------------------------------
```

FIG.9B-3

```
1310  GGAAGAATAA ATTAGAGAAA AACTGGAATG ACTGAATCGG AACAAGGCAA
      CCTTCTTATT TAATCTCTTT TTGACCTTAC TGACTTAGCC TTGTTCCGTT

1360  AGGCTATAAA AAAAATTAAG CAGCAGTATC CTCTTGGGGG CCCCTTCCCC
      TCCGATATTT TTTTTAATTC GTCGTCATAG GAGAACCCCC GGGGAAGGGG

1410  ACACTATCTC AATGCAAATA TCTGTCTGAA ACGGTCCCTG GCTAAACTCC
      TGTGATAGAG TTACGTTTAT AGACAGACTT TGCCAGGGAC CGATTTGAGG

        NcoI
       ~~~~~~
1460  ACCCATGGGT TGGCCAGCCT TGCCTTGACC AATAGCCTTG ACAAGGCAAA
      TGGGTACCCA ACCGGTCGGA ACGGAACTGG TTATCGGAAC TGTTCCGTTT

1510  CTTGACCAAT AGTCTTAGAG TATCCAGTGA GGCCAGGGGC CGGCGGCTGG
      GAACTGGTTA TCAGAATCTC ATAGGTCACT CCGGTCCCCG GCCGCCGACC

1560  CTAGGGATGA AGAATAAAAG GAAGCACCCT TCAGCAGTTC CACACACTCG
      GATCCCTACT TCTTATTTTC CTTCGTGGGA AGTCGTCAAG GTGTGTGAGC

                                                  NcoI
                                                 ~~~~~~
1610  CTTCTGGAAC GTCTGAGATT ATCAATAAGC TCCTAGTCCA GACGCCATGG
      GAAGACCTTG CAGACTCTAA TAGTTATTCG AGGATCAGGT CTGCGGTACC

1660  GTCATTTCAC AGAGGAGGAC AAGGCTACTA TCACAAGCCT GTGGGGCAAG
      CAGTAAAGTG TCTCCTCCTG TTCCGATGAT AGTGTTCGGA CACCCCGTTC
```

FIG.9B-4

```
1710  GTGAATGTGG AAGATGCTGG AGGAGAAACC CTGGGAAGGT AGGCTCTGGT
      CACTTACACC TTCTACGACC TCCTCTTTGG GACCCTTCCA TCCGAGACCA
------------------------------------------------------------
1760  GACCAGGACA AGGGAGGGAA GGAAGGACCC TGTGCCTGGC AAAAGTCCAG
      CTGGTCCTGT TCCCTCCCTT CCTTCCTGGG ACACGGACCG TTTTCAGGTC
------------------------------------------------------------
1810  GTCGCTTCTC AGGATTTGTG GCACCTTCTG ACTGTCAAAC TGTTCTTGTC
      CAGCGAAGAG TCCTAAACAC CGTGGAAGAC TGACAGTTTG ACAAGAACAG
------------------------------------------------------------
                                     NcoI
                                     ~~~~~~
1860  AATCTCACAG GCTCCTGGTT GTCTACCCAT GGACCCAGAG GTTCTTTGAC
      TTAGAGTGTC CGAGGACCAA CAGATGGGTA CCTGGGTCTC CAAGAAACTG
------------------------------------------------------------
1910  AGCTTTGGCA ACCTGTCCTC TGCCTCTGCC ATCATGGGCA ACCCCAAAGT
      TCGAAACCGT TGGACAGGAG ACGGAGACGG TAGTACCCGT TGGGGTTTCA
------------------------------------------------------------
1960  CAAGGCACAT GGCAAGAAGG TGCTGACTTC CTTGGGAGAT GCCATAAAGC
      GTTCCGTGTA CCGTTCTTCC ACGACTGAAG GAACCCTCTA CGGTATTTCG
------------------------------------------------------------
2010  ACCTGGATGA TCTCAAGGGC ACCTTTGCCC AGCTGAGTGA ACTGCACTGT
      TGGACCTACT AGAGTTCCCG TGGAAACGGG TCGACTCACT TGACGTGACA
------------------------------------------------------------
                      BamHI
                      ~~~~~~
2060  GACAAGCTGC ATGTGGATCC TGAGAACTTC AGGGTGAGTC TATGGGACCC
      CTGTTCGACG TACACCTAGG ACTCTTGAAG TCCCACTCAG ATACCCTGGG
------------------------------------------------------------
```

FIG.9B-5

```
2110  TTGATGTTTT CTTTCCCCTT CTTTTCTATG GTTAAGTTCA TGTCATAGGA
      AACTACAAAA GAAAGGGGAA GAAAAGATAC CAATTCAAGT ACAGTATCCT
-----------------------------------------------------------
2160  AGGGGAGAAG TAACAGGGTA CAGTTTAGAA TGGGAAACAG ACGAATGATT
      TCCCCTCTTC ATTGTCCCAT GTCAAATCTT ACCCTTTGTC TGCTTACTAA
-----------------------------------------------------------
2210  GCATCAGTGT GGAAGTCTCA GGATCGTTTT AGTTTCTTTT ATTTGCTGTT
      CGTAGTCACA CCTTCAGAGT CCTAGCAAAA TCAAAGAAAA TAAACGACAA
-----------------------------------------------------------
2260  CATAACAATT GTTTTCTTTT GTTTAATTCT TGCTTTCTTT TTTTTTCTTC
      GTATTGTTAA CAAAAGAAAA CAAATTAAGA ACGAAAGAAA AAAAAAGAAG
-----------------------------------------------------------
2310  TCCGCAATTT TTACTATTAT ACTTAATGCC TTAACATTGT GTATAACAAA
      AGGCGTTAAA AATGATAATA TGAATTACGG AATTGTAACA CATATTGTTT
-----------------------------------------------------------
2360  AGGAAATATC TCTGAGATAC ATTAAGTAAC TTAAAAAAAA ACTTTACACA
      TCCTTTATAG AGACTCTATG TAATTCATTG AATTTTTTTT TGAAATGTGT
-----------------------------------------------------------
2410  GTCTGCCTAG TACATTACTA TTTGGAATAT ATGTGTGCTT ATTTGCATAT
      CAGACGGATC ATGTAATGAT AAACCTTATA TACACACGAA TAAACGTATA
-----------------------------------------------------------
2460  TCATAATCTC CCTACTTTAT TTTCTTTTAT TTTTAATTGA TACATAATCA
      AGTATTAGAG GGATGAAATA AAAGAAAATA AAAATTAACT ATGTATTAGT
-----------------------------------------------------------
2510  TTATACATAT TTATGGGTTA AAGTGTAATG TTTTAATATG TGTACACATA
      AATATGTATA AATACCCAAT TTCACATTAC AAAATTATAC ACATGTGTAT
-----------------------------------------------------------
```

FIG.9B-6

```
2560  TTGACCAAAT CAGGGTAATT TTGCATTTGT AATTTTAAAA AATGCTTTCT
      AACTGGTTTA GTCCCATTAA AACGTAAACA TTAAAATTTT TTACGAAAGA

2610  TCTTTTAATA TACTTTTTTG TTTATCTTAT TTCTAATACT TTCCCTAATC
      AGAAAATTAT ATGAAAAAAC AAATAGAATA AAGATTATGA AAGGGATTAG

2660  TCTTTCTTTC AGGGCAATAA TGATACAATG TATCATGCCT CTTTGCACCA
      AGAAAGAAAG TCCCGTTATT ACTATGTTAC ATAGTACGGA GAAACGTGGT

2710  TTCTAAAGAA TAACAGTGAT AATTTCTGGG TTAAGGCAAT AGCAATATTT
      AAGATTTCTT ATTGTCACTA TTAAAGACCC AATTCCGTTA TCGTTATAAA

2760  CTGCATATAA ATATTTCTGC ATATAAATTG TAACTGATGT AAGAGGTTTC
      GACGTATATT TATAAAGACG TATATTTAAC ATTGACTACA TTCTCCAAAG

2810  ATATTGCTAA TAGCAGCTAC AATCCAGCTA CCATTCTGCT TTTATTTTAT
      TATAACGATT ATCGTCGATG TTAGGTCGAT GGTAAGACGA AAATAAAATA

2860  GGTTGGGATA AGGCTGGATT ATTCTGAGTC CAAGCTAGGC CCTTTTGCTA
      CCAACCCTAT TCCGACCTAA TAAGACTCAG GTTCGATCCG GGAAAACGAT

2910  ATCATGTTCA TACCTCTTAT CTTCCTCCCA CAGCTCCTGG GCAACGTGCT
      TAGTACAAGT ATGGAGAATA GAAGGAGGGT GTCGAGGACC CGTTGCACGA

                                        EcoRI
                                        ~~~~~~
2960  GGTCTGTGTG CTGGCCCATC ACTTTGGCAA AGAATTCACC CCTGAGGTGC
      CCAGACACAC GACCGGGTAG TGAAACCGTT TCTTAAGTGG GGACTCCACG
```

FIG.9B-7

```
3010  AGGCTTCCTG GCAGAAGATG GTGACTGCAG TGGCCAGTGC CCTGTCCTCC
      TCCGAAGGAC CGTCTTCTAC CACTGACGTC ACCGGTCACG GGACAGGAGG

3060  AGATACCACT GAGCCTCTTG CCCATGATTC AGAGCTTTCA AGGATAGGCT
      TCTATGGTGA CTCGGAGAAC GGGTACTAAG TCTCGAAAGT TCCTATCCGA

3110  TTATTCTGCA AGCAATACAA ATAATAAATC TATTCTGCTG AGAGATCACA
      AATAAGACGT TCGTTATGTT TATTATTTAG ATAAGACGAC TCTCTAGTGT

3160  CATGATTTTC TTCAGCTCTT TTTTTTACAT CTTTTTAAAT ATATGAGCCA
      GTACTAAAAG AAGTCGAGAA AAAAAATGTA GAAAAATTTA TATACTCGGT

3210  CAAAGGGTTT ATATTGAGGG AAGTGTGTAT GTGTATTTCT GCATGCCTGT
      GTTTCCCAAA TATAACTCCC TTCACACATA CACATAAAGA CGTACGGACA

3260  TTGTGTTTGT GGTGTGTGCA TGCTCCTCAT TTATTTTTAT ATGAGATGTG
      AACACAAACA CCACACACGT ACGAGGAGTA AATAAAAATA TACTCTACAC

3310  CATTTTGATG AGCAAATAAA AGCAGTAAAG ACACTTGTAC ACGGGAGTTC
      GTAAAACTAC TCGTTTATTT TCGTCATTTC TGTGAACATG TGCCCTCAAG

3360  TGCAAGTGGG AGTAAATGGT GTTGGAGAAA TCCGGTGGGA AGAAAGACCT
      ACGTTCACCC TCATTTACCA CAACCTCTTT AGGCCACCCT TCTTTCTGGA

3410  CTATAGGACA GGACTTCTCA GAAACAGATG TTTTGGAAGA GATGGGAAAA
      GATATCCTGT CCTGAAGAGT CTTTGTCTAC AAAACCTTCT CTACCCTTTT
```

FIG.9B–8

```
3460  GGTTCAGTGA AGACCTGGGG GCTGGATTGA TTGCAGCTGA GTAGCAAGGA
      CCAAGTCACT TCTGGACCCC CGACCTAACT AACGTCGACT CATCGTTCCT
--------------------------------------------------------------
                                  NheI
                                 ~~~~~~~~
3510  TGGTTCTTAA TGAAGGGAAA GTGTTCCAGC TAGCGTGCTA GTCTCCCGGA
      ACCAAGAATT ACTTCCCTTT CACAAGGTCG ATCGCACGAT CAGAGGGCCT
--------------------------------------------------------------
3560  ACTATCACTC TTTCACAGTC TGCTTTGGAA GGACTGGGCT TAGTATGAAA
      TGATAGTGAG AAAGTGTCAG ACGAAACCTT CCTGACCCGA ATCATACTTT
--------------------------------------------------------------
3610  AGTTAGGACT GAGAAGAATT TGAAAGGGGG CTTTTTGTAG CTTGATATTC
      TCAATCCTGA CTCTTCTTAA ACTTTCCCCC GAAAAACATC GAACTATAAG
--------------------------------------------------------------
3660  ACTACTGTCT TATTACCCTA TCATAGGCCC ACCCCAAATG GAAGTCCCAT
      TGATGACAGA ATAATGGGAT AGTATCCGGG TGGGGTTTAC CTTCAGGGTA
--------------------------------------------------------------
3710  TCTTCCTCAG GATGTTTAAG ATTAGCATTC AGGAAGAGAT CAGAGGTCTG
      AGAAGGAGTC CTACAAATTC TAATCGTAAG TCCTTCTCTA GTCTCCAGAC
--------------------------------------------------------------
                                        NheI   EcoRV
                                       ~~~~~~~~~~~~~~
3760  CTGGCTCCCT TATCATGTCC CTTATGGTGC TTCTGGCTAG CGATATCACC
      GACCGAGGGA ATAGTACAGG GAATACCACG AAGACCGATC GCTATAGTGG
--------------------------------------------------------------
3810  GGTAT
      CCATA
--------------------------------------------------------------
```

FIG.9B-9

HYBRID NUCLEIC ACID MOLECULES AND VECTORS INCLUDING β-GLOBIN REGULATORY ELEMENTS

CROSS REFERENCE TO RELATED APPLICATION

This application claims priority from Canadian application no. 2,246,005, filed on Oct. 1, 1998, which is incorporated by reference in its entirety.

FIELD OF THE INVENTION

The invention relates to hybrid nucleic acid molecules and vectors for expression, at single copy, of RNA, polypeptides and for gene therapy in erythroid and other cells. In particular, the invention relates to hybrid nucleic acid molecules and vectors that are useful for treatment of hemoglobinopathies such as sickle cell anemia and β- or α-thalassemia.

The invention also relates to hybrid nucleic acid molecules that are useful for erythroid expression at single copy of RNA and polypeptides in transgenic animals.

BACKGROUND OF THE INVENTION

One difficult aspect of gene therapy is in reproducibly obtaining high-level, tissue-specific, and long-term expression from nucleic acid molecules transferred into stem cells [1]. Since commonly used retrovirus and Adeno-Associated Virus (AAV) vectors may integrate at single copy, their transduced nucleic acid molecules should be regulated by tissue-specific elements that function at single copy. Locus Control Regions (LCR) are well suited for this task as they direct reproducible expression from all integration sites and transgene copy numbers[2], indicating that they have transcriptional enhancement and chromatin opening activities. For example, the human β-globin LCR directs high level β-globin transgene expression in erythroid cells of transgenic mice regardless of the integration site. However, it has become apparent that the β-globin LCR cannot confer reproducible transgene expression in mice on other nucleic acid molecule sequences such as the LacZ marker gene [3, 4], γ-globin genes [5–7], or even β-globin genes that lack a 3' element [8, 9]. These findings suggest that chromatin opening by the LCR requires β-globin gene sequences, and that the utility of this LCR is limited to expression of the β-globin gene. It is not clear what gene sequences would be useful. In contrast to expression in transgenic mice, chromatin opening activities are not required for transient expression [4] or for stable expression when under selection for a drug resistance gene [10]. Therefore, such in vitro assays are not well suited for the evaluation of minigene cassettes for use in retrovirus-mediated gene therapy.

Efficient cell-specific nucleic acid molecule expression at some but not all transgene integration sites can be achieved by using cell-specific gene proximal elements including promoter elements, cell-specific regulatory elements such as enhancers and silencers, RNA processing signals, and cell-specific RNA-stabilizing elements. Cell-specific gene expression at all transgene integration sites primarily results from locus control regions (LCRs). However, it is considered to be very difficult to design a hybrid nucleic acid molecule that expresses at all integration sites for gene therapy of erythroid cells or their precursors because there is inadequate information about regulation of erythroid gene expression by LCRs and of the requirement by LCRs for specific gene proximal elements. Currently, no suitable hybrid nucleic acid molecule that expresses at single copy at all transgene integration sites for erythroid or precursor cell gene therapy has been reported.

SUMMARY OF THE INVENTION

The invention is a hybrid nucleic acid molecule for expressing RNA and polypeptides specifically in cells of the erythroid lineage. It is particularly useful for gene therapy of diseases such as thalassemias and sickle cell anemia by delivery of therapeutically useful globin proteins in erythroid cells. Other RNA and polypeptides may also be delivered with the hybrid nucleic acid molecules for gene therapy or in transgenic animals.

The invention uses human β-globin DNA regulatory elements to obtain high level, reproducible, tissue specific, single copy expression of coding nucleic acid molecules. Unlike past attempts to use β-globin DNA regulatory elements in preparing vectors, the invention uses much smaller portions of β-globin DNA regulatory elements. The simultaneous presence of the β-globin promoter, intron 2 and 3' enhancer and the 5'HS3 is sufficient to provide coding nucleic acid molecule expression, for example the γ-globin gene. The hybrid nucleic acid molecule is suitable for DNA or viral mediated gene therapy of sickle cell anemias and thalassemias.

The invention also includes an isolated nucleic acid molecule comprising β-globin DNA regulatory elements that is capable of having a coding nucleic acid molecule inserted in it. The molecule is capable of directing production of a polypeptide at single copy in a targeted cell of the erythroid lineage.

In a preferred embodiment, the invention relates to hybrid nucleic acid molecules for gene therapy in erythroid and other cells, and in particular α-, β- δ-, ε-, γ-, or ζ-globin nucleotide sequences, or derivatives thereof, operably linked to β-globin regulatory elements. The hybrid nucleic acid molecules are useful for treatment of hemoglobinopathies such as sickle cell anemia or β- or α-thalassemia.

The invention also includes a hybrid nucleic acid molecule for producing a protein in a targeted cell, preferably an erythroid cell, consisting of:

β-globin DNA regulatory elements, and a nucleic acid molecule operatively associated with the regulatory elements and capable of expression in the cell.

Other hemoglobinopathy or erythroid diseases, disorders or abnormal physical states that require erythroid specific expression may also be treated. They are useful for expressing any genes in cells of the erythroid lineage in mammals, such as mice or human, such as genes encoding Glucose 6 Phosphate Dehydrogenase or ferrochelatase polypeptides. Marker genes may also be used, such as green fluorescent protein.

In a preferred embodiment, the hybrid nucleic acid molecule consists of all or part of the nucleotide sequence of the BGT50 construct shown in FIG. 8. The β-globin DNA regulatory elements are preferably human β-globin DNA regulatory elements. The regulatory elements are preferably a 5'HS3, a promoter, a 3' enhancer and intron 2.

The invention also includes a composition, preferably a pharmaceutical composition, including a therapeutically effective amount of the hybrid nucleic acid molecule and a pharmaceutically acceptable carrier. Another embodiment of the invention relates to a composition comprising the hybrid nucleic acid molecule and a carrier.

In another embodiment, the invention relates to the use of a hybrid nucleic acid molecule for treatment of a disease, disorder or abnormal physical state, including hemoglobinopathy. Another embodiment of the invention includes a method of medical treatment of hemoglobinopathy comprising administering a hybrid nucleic acid molecule to a patient and expressing the nucleic acid molecule.

The invention also includes a method of designing a hybrid nucleic acid molecule for treatment of a hemoglobinopathy. The method involves generating a series of hybrid nucleic acid molecules including erythroid cell-specific regulatory elements and then assessing each hybrid nucleic acid molecule single copy transgenic mice for the expression of reporter nucleic acid molecules or the hybrid nucleic acid molecule.

The invention includes a hybrid nucleic acid molecule for treating a defect in a globin gene in a cell of an erythroid lineage, the hybrid nucleic acid molecule including: a) β-globin gene regulatory elements which elements are capable of regulating gene expression in the cell; and b) a coding nucleic acid molecule operatively associated with the regulatory elements and capable of expression in the cell, the coding nucleic acid molecule encoding a globin protein or a derivative thereof having globin activity. The defect being treated causes a hemoglobinopathy. The target cell may be an erythroid cell. The invention also includes a cell of an erythroid lineage containing recombinant β-globin DNA regulatory elements and a coding nucleic acid molecule operatively associated with the regulatory elements, the cell expressing polypeptides, such as globins, not normally expressed by the cell at biologically significant levels.

Another aspect of the invention includes DNA sequences which are complementary to the aforementioned sequences.

Another embodiment of the invention relates to a hybrid nucleic acid molecule that at single copy is capable of producing a RNA and a polypeptide in a targeted mammalian cell of the erythroid lineage, including:

β-globin DNA regulatory elements, and a coding nucleic acid molecule operatively associated with the regulatory elements and capable of expression in the cell.

The hybrid nucleic acid molecule CAN INCLUDE all or part of a nucleic acid molecule selected from th group consisting of a) SEQ ID NO:1 or SEQ ID NO:2, or a complement thereof b) SEQ ID NO:3 or SEQ ID NO:4, or a complement thereof c) a nucleic acid molecule that hybridizes to all or part of a nucleic acid molecule shown in SEQ ID NO:1–SEQ ID NO:4, or a complement thereof under high stringency hybridization conditions; and d) a nucleic acid molecule having at least 70% identity with the nucleotide sequence of (a) or (b).

The mammal is preferably a human. The β-globin DNA regulatory elements may include 5'HS3, a β-globin promoter, a β-globin intron 2 and a β-globin 3' enhancer. In another embodiment the β-globin DNA regulatory elements may include an 5'HS3, Aγ-globin promoter, a β-globin intron 2 and a β-globin 3' enhancer. The coding sequence preferably encodes a globin polypeptide or a derivative thereof having globin activity, such as α-, β-, δ-, ε-, γ- or ζ-globin. The β-globin DNA regulatory elements may include human β-globin DNA regulatory elements. The regulatory elements may include a 5'HS3, a promoter, a 3' enhancer and intron 2.

The hybrid nucleic acid molecule preferably includes 5'-A-X-Y-C-D-3' wherein A is a 5'HS3, X includes a β-globin promoter or an Aγ-globin promoter, Y includes a coding nucleic acid molecule, C includes a β-globin intron 2, and D includes a β-globin 3' enhancer. The coding nucleic acid molecule preferably encodes a globin polypeptide or a derivative thereof having globin activity.

The invention also includes a vector including a nucleic acid molecule of the invention. The invention also includes a composition including a vector or nucleic acid molecule of the invention. Another aspect of the invention is a host cell including a vector or nucleic acid molecule of the invention. The host cell can include a cell of the erythroid lineage selected from the group including an erythroid cell, an erythroid cell precursor, a bone marrow cell, an umbilical cord blood cell, a hematopoietic stem cell, a hematopoietic stem cell that is CD34−/CD38−, or CD34+/CD38−, a progenitor cell of the erythroid lineage, CFU-GEMM, BFU-E, CFU-E, a pro-erythroblast, an erythroblast and an erythrocyte.

BRIEF DESCRIPTION OF THE DRAWINGS

Sequence identification numbers (SEQ ID NO;) in the figures refer to the 5' to 3' strand. Preferred embodiments of the invention will be described in relation to the drawings in which.

Figure 1:
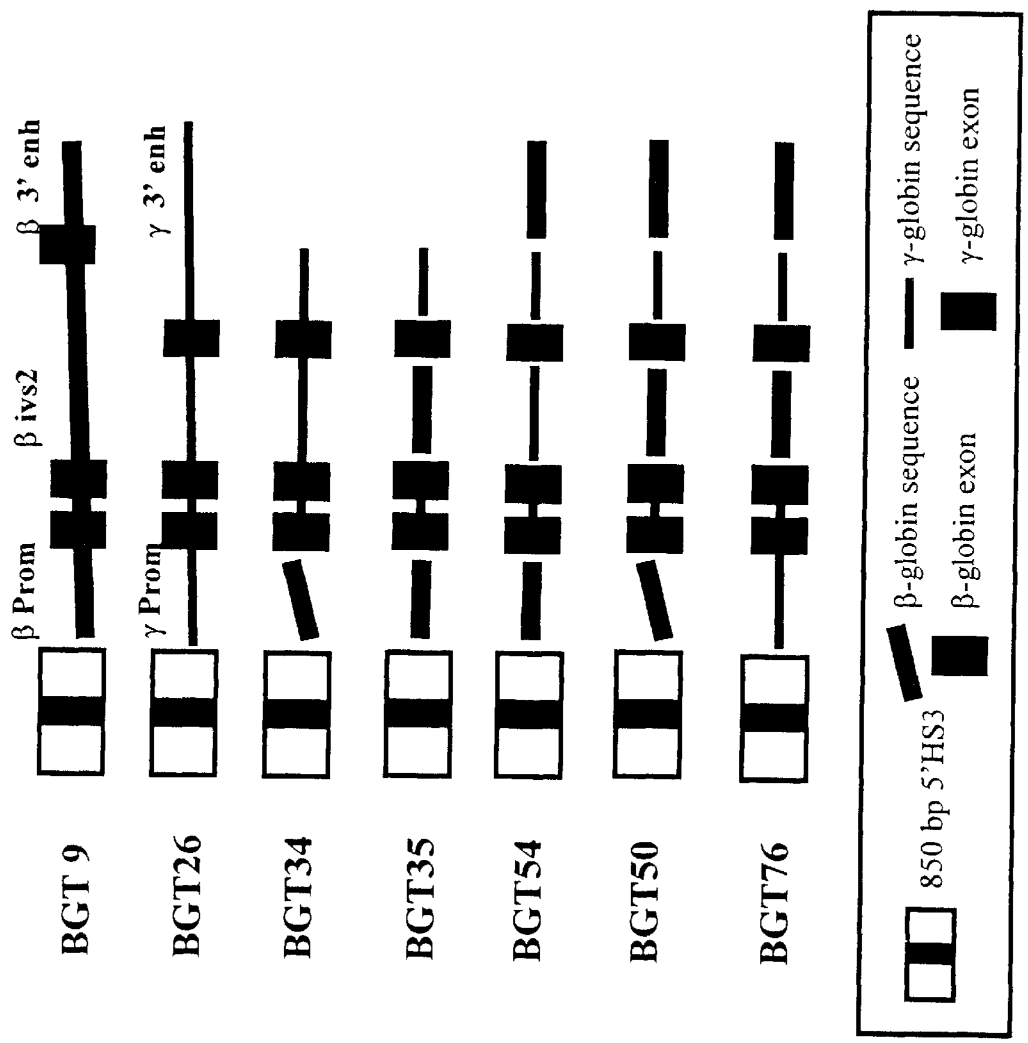
FIG. 1

5'HS3-linked β-globin, γ-globin, and β/γ-globin hybrid constructs used to determine which β-globin sequences are required by 5'HS3 to activate single-copy transgenes. RNA levels from each construct was analyzed in the fetal liver of 15.5 day single-copy transgenic founder mice. BGT9 was designed to determine if the 850 bp 5'HS3 fragment could activate single-copy β-globin transgenes. BGT26 was designed to determine if 5'HS3 could similarly activate single-copy γ-globin transgenes or whether a functional interaction between 5'HS3 and β-globin sequences was necessary for single-copy transgene activation. The series of β/γ-globin transgenes that follow were designed to illustrate which β-globin sequences are required for single-copy transgene activation by 5'HS3. βProm, β-globin promoter; γProm, γ-globin promoter; βivs2, β-globin intron 2; β3'enh, β-globin 3' enhancer; MAR, matrix attachment region within β-globin intron 2.

FIG. 2

Expression of human globin mRNA in transgenic mice containing the BGT9 construct. S1 nuclease analysis on fetal liver RNA of 15.5 day $F_0$ BGT9 transgenic mice showing that BGT9 is expressed in all 17 animals including 3 single-copy mice. These data show that the 850 bp 5'HS3 element can express reproducible levels of β-globin transcripts. Hβ, human β-globin protected probe fragment; Mβ, mouse β major protected probe fragment; N, nontransgenic; μD, one copy μD14 microlocus line (discussed in text).

FIG. 3

Expression of human globin mRNA in transgenic mice containing the BGT26 and BGT34 constructs. S1 nuclease analysis on fetal liver RNA of 15.5 day $F_0$ transgenic mice showing that BGT26 is expressed to low or undetectable levels and that BGT34 is expressed to significant levels in 4/7 transgenic mice. These data show that β-globin gene sequences are required for reproducible single-copy transgene activation by 5'HS3 and that the β-globin promoter element is not sufficient for this activity. Hγ, human Aγ-globin protected probe fragment; Mβ, mouse β major protected probe fragment; N, nontransgenic; C, 50–48, the highest expressing BGT50 single-copy transgenic mouse (discussed in text; see FIG. 6); 3X, probe excess control. Copy #=1*, one intact copy plus a partial copy of the transgene.

FIG. 4

Expression of human globin mRNA in transgenic mice containing the BGT35 construct. S1 nuclease analysis on fetal liver RNA of 15.5 day $F_0$ transgenic mice showing BGT35 is expressed to significant levels in 5/7 transgenic mice. These data show that the β-globin promoter element and intron 2 sequence are not sufficient for reproducible single-copy transgene expression. Hγ, human Aγ-globin protected probe fragment; Mβ, mouse β major protected probe fragment; N, nontransgenic; C, 50–48, the highest expressing BGT50 single-copy transgenic mouse (discussed in text, see FIG. 6); 3X, probe excess control.

FIG. 5

Expression of human globin mRNA in transgenic mice containing the BGT54 construct. S1 nuclease analysis on fetal liver RNA of 15.5 day $F_0$ transgenic mice showing that BGT54 is expressed to significant levels in 13/15 transgenic mice. These data show that the β-globin promoter element and 3' enhancer sequence are not sufficient for reproducible single-copy transgene expression. Hγ, human Aγ-globin protected probe fragment; Mβ, mouse β major protected probe fragment; N, nontransgenic; C, 50–48, the highest expressing BGT50 single-copy transgenic mouse (discussed in text, see FIG. 6); Copy #=1*, one intact copy plus a partial copy of the transgene.

FIG. 6

Expression of human globin mRNA in transgenic mice containing the BGT50 construct. S1 nuclease analysis on fetal liver RNA of 15.5 day $F_0$ transgenic mice showing that BGT50 is expressed in all 8 animals including 7 single-copy mice. These data show that the β-globin intron 2 and 3' enhancer elements are sufficient for reproducible transgene expression when linked to the 5'HS3 element and the β-globin promoter. Hγ, human Aγ-globin protected probe fragment; Mβ, mouse β major protected probe fragment; N, nontransgenic; C, 50–48, the highest expressing BGT50 single-copy transgenic mouse; Copy #=1*, one intact copy plus a partial copy of the transgene.

FIG. 7

Expression of human globin mRNA in transgenic mice containing the BGT76 construct. S1 nuclease analysis on fetal liver RNA of 15.5 day $F_0$ transgenic mice showing that BGT76 is expressed in all 17 animals including 5 single-copy mice. These data show that activation of single-copy transgenes by a functional interaction between 5'HS3, the β-globin intron 2, and 3' enhancer elements is not specific for the β-globin promoter. Hγ, human Aγ-globin protected probe fragment; Mβ, mouse β major protected probe fragment; N, nontransgenic; C, 50–48, the highest expressing BGT50 single-copy transgenic mouse (discussed in text, see FIG. 6); Copy #=1*, one intact copy plus a partial copy of the transgene.

FIG. 8

FIG. 8A shows the sequence of SEQ ID NO:1.

In a preferred embodiment, the figure shows DNA nucleotide sequence of the BGT50 construct including the human β/γ-globin hybrid nucleic acid molecule of the invention, and the 5'HS3 element.

FIG. 8B shows the sequence of SEQ ID NO:2.

In a preferred embodiment, the figure shows DNA nucleotide sequence of the BGT50 construct including a coding sequence, the human β/γ-globin hybrid nucleic acid molecule of the invention, and the 5'HS3 element.

FIG. 9

FIG. 9A shows the sequences of SEQ ID NO:3.

In a preferred embodiment, the figure shows DNA nucleotide sequence of the BGT76 construct including the human β/γ-globin hybrid nucleic acid molecule of the invention, and the 5'HS3 element, FIG. 9B shows the sequences of SEQ ID NO:4.

In a preferred embodiment, the figure shows DNA nucleotide sequence of the BGT76 construct including a coding sequence, the human β/γ-globin hybrid nucleic acid molecule of the invention, and the 5'HS3 element.

FIG. 10

This figure shows a preferred embodiment of the hybrid nucleic acid molecule of the invention, as well as variations.

Maps of BGT50 and BGT76 constructs defining critical regulatory elements. According to the BGT50 sequence, the coordinates of these regulatory elements are as follows: A about 850 bp 5'HS3 (about 28–882 bp); B about 815 bp β-globin promoter and the 5'UTR (about 903–1771 bp); C β-globin intron 2 (2191–3108 bp); D β-globin 3' enhancer (about 3655–3912 bp). BGT 76 contains A, C and D elements but not the β element which has been replaced with the Aγ-globin promoter (E element). According to the BGT 76 sequence, the coordinates of these regulatory elements are as follows: A (about 23–877 bp); E about 700 bp Aγ-globin promoter and 5'UTR (about 896–1655 bp); C (about 2075–2992 bp); D (about 3539–3796 bp).

DETAILED DESCRIPTION OF THE INVENTION

The invention satisfies the need for suitable hybrid nucleic acid molecules for erythroid and precursor cell gene therapy treatment of hemoglobinopathies. The hybrid nucleic acid molecules contain human β-globin DNA regulatory elements which naturally express therapeutic polypeptides, preferably, α-, β- δ-, ϵ-, γ-, or ζ-globin polypeptides or their derivatives having globin activity. The hybrid nucleic acid molecules direct a high level of nucleic acid molecule expression in vitro and in vivo. The hybrid nucleic acid molecules are safe and confer a sustained and appropriate level of cell-specific expression for gene therapy. The hybrid nucleic acid molecules may be used in cells of the erythroid lineage, such as erythroid cells or their precursors, bone marrow, umbilical cord blood cells, or cells sorted from them including hematopoietic stem cells that are CD34−/CD38−, or CD34+/CD38−, progenitor cells of the erythroid lineage such as CFU-GEMM, BFU-E and CFU-E, or erythroid cells such as pro-erythroblasts, erythroblasts, or erythrocytes. The cells are preferably mammalian cells (eg. murine cells) and more preferably human cells. Globin genes are known in the art. The sequences described in this application (including regulatory elements) as well as globin derivatives may be readily obtained from a number of sources, such as Genbank (National Center for Biotechnology Information, USA or the Globin Gene Server Databases (Laboratories of Computer Science & Engineering and Biochemistry & Molecular Biology at the Pennsylvania State University, USA.

Figure 10:
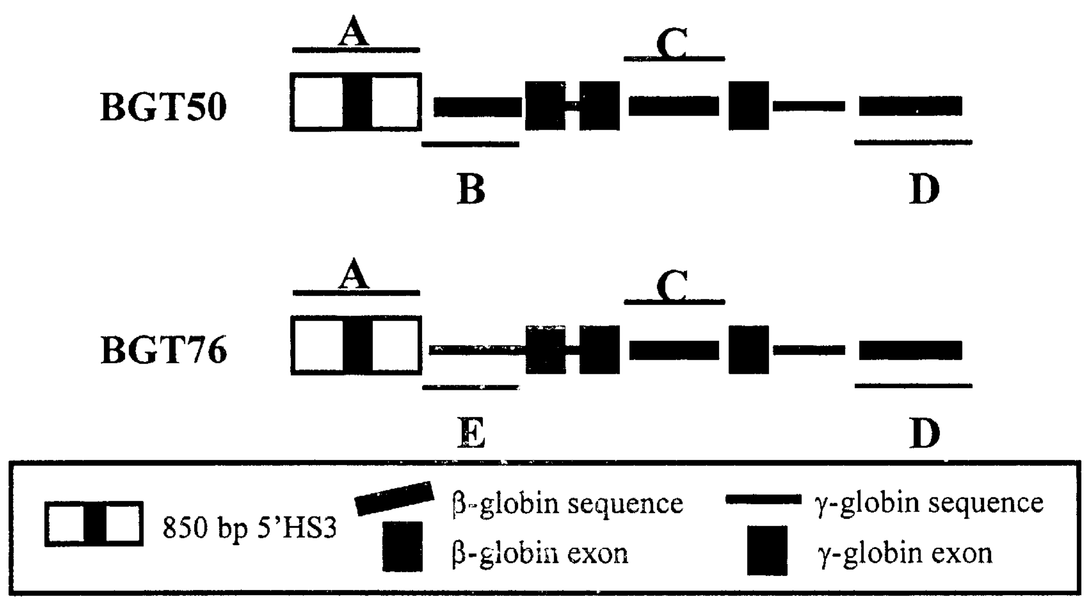

In a preferred embodiment, the hybrid nucleic acid molecules may be as shown in FIG. 10. This figure provides maps of the preferred BGT50 and BGT76 constructs showing the regulatory elements. A generic sequence is as follows: 5'-A-X-C-D-3', wherein A includes a 5'HS3, X includes a B-globin promoter or an Aγ-globin promoter, C includes a β-globin intron 2 and D includes a β-globin 3' enhancer. These sequences may be modified. Additional regulatory elements may also be used and these will be apparent to a person skilled in the art.

More preferably the generic sequence is 5'-A-X-Y-C-D-3' wherein A is a 5'HS3, X includes a β-globin promoter or an Aγ-globin promoter, Y includes a coding nucleic acid molecule of interest (preferably a γ-globin sequence, another globin gene or a derivative thereof), C includes a β-globin intron 2 and D includes a β-globin 3' enhancer. These sequences may be modified. Additional regulatory elements may also be used and these will be apparent to a person skilled in the art.

The invention includes a method for delivering a gene encoding a globin polypeptide to the cells of an individual with a hemoglobinopathy, comprising administering to the individual a vector comprising a hybrid nucleic acid molecule including a coding nucleic acid molecule encoding a globin polypeptide or a derivative thereof.

The invention also includes a method for providing an individual having a hemoglobinopathy with biologically active globin protein, comprising administering to the individual a vector comprising a hybrid nucleic acid molecule including a coding nucleic acid molecule encoding a globin polypeptide or a derivative thereof.

The invention also includes a method for producing a stock of recombinant virus comprising a hybrid nucleic acid molecule including a coding nucleic acid molecule encoding a globin polypeptide or a derivative thereof.

Hybrid Nucleic Acid Molecules

The invention relates to hybrid nucleic acid molecules for expressing coding nucleic acid molecules (the term "coding nucleic acid molecule" includes the term "transgene") that produce globin polypeptides in cells of the erythroid lineage. The globin polypeptides are preferably, α-, β- α-, ε-, γ-, or ζ-globin polypeptides or their derivatives having globin activity such that the globin is capable of forming part of a hemoglobin complex for transporting oxygen. Examples of globin derivatives are described in U.S. Pat. No. 5,861,488 (LeBoulch and London, issued to MIT) which is incorporated by reference in its entirety. The hybrid nucleic acid molecules are also useful for expressing other nucleic acid molecules of interest. The hybrid nucleic acid molecules are preferably constructed from human β-globin DNA regulatory elements that naturally express nucleic acid molecules in cells of the erythroid lineage. The regulatory element sequences may be modified according to known techniques while retaining the desired activities. These , β-globin DNA regulatory elements are used to direct the expression of coding nucleic acid molecules for use in research, protein production and gene therapy in cells of the erythroid lineage. Since the hybrid nucleic acid molecules use mammalian (murine or more preferably human) DNA regulatory elements that are specifically expressed in cells of the erythroid lineage, high levels of protein expression are produced.

Other preferred coding nucleic acid molecules include 1) a nucleic acid molecule having at least about 70% sequence identity to a β-globin nucleic acid molecule, a γ-globin nucleic acid molecule, a δ-globin nucleic acid molecule, a ε-globin nucleic acid molecule, a ζ-globin nucleic acid molecule and an α-globin nucleic acid molecule and encoding a protein having β-globin, γ-globin, δ-globin, ε-globin, ζ-globin or α-globin activity, respectively, and 2) a nucleic acid molecule encoding a protein having β-globin, γ-globin, ε-globin, ζ-globin, ζ-globin, or α-globin activity, such that the globin is capable of forming part of a hemoglobin complex for transporting oxygen. Changes in the nucleotide sequence which result in production of a chemically equivalent (for example, as a result of redundancy of the genetic code) or chemically similar amino acid (for example where sequence similarity is present), may also be made to produce therapeutic polypeptides using the hybrid nucleic acid molecules of the invention.

The hybrid nucleic acid molecules may be used in vivo or in vitro. Cells transfected or transduced in vitro can be used for ex vivo gene therapy or as a research tool or for protein production. The hybrid nucleic acid molecules are also useful for gene therapy by transfecting or transducing cells in vivo to express a therapeutic protein. Gene therapy may be used to treat diseases, disorders or abnormal physical states of cells of the erythroid lineage, such as hemoglobinopathies. For example, if one were to upregulate the expression of a gene, one could insert the sense sequence into the hybrid nucleic acid molecule. If one were to downregulate the expression of the gene, one could insert the antisense sequence into the expression cassette. Techniques for inserting sense and antisense sequences (or fragments of these sequences) would be apparent to those skilled in the art. The nucleic acid molecule or nucleic acid molecule fragment may be either isolated from a native source (in sense or antisense orientations) or synthesized. It may also be a mutated native or synthetic sequence or a combination of these.

Variations of Hybrid Nucleic Acid Molecules

Modifications

Many modifications may be made to the hybrid nucleic acid molecule DNA sequences disclosed in this application and these will be apparent to one skilled in the art. The invention includes nucleotide modifications of the sequences disclosed in this application (or fragments thereof) that are capable of directing single copy expression in cells of the erythroid lineage. For example, a β-globin regulatory sequences may be modified or a nucleic acid sequence to be expressed may be modified using techniques known in the art. Modifications include substitution, insertion or deletion of nucleotides or altering the relative positions or order of nucleotides.

Sequence Identity

The hybrid nucleic acid molecules of the invention also include nucleic acid molecules (or a fragment thereof) having at least about: 70% identity, at least 80% identity, at least 90% identity, at least 95% identity, at least 96% identity, at least 97% identity, at least 98% identity or, most preferred, at least 99% or 99.5% identity to a hybrid nucleic acid molecule of the invention and which are capable of single copy expression of nucleic acid molecules in cells of the erythroid lineage. Identity refers to the similarity of two nucleotide sequences that are aligned so that the highest order match is obtained. Identity is calculated according to methods known in the art. For example, if a nucleotide sequence (called "Sequence A") has 90% identity to a portion of SEQ ID NO: 1, then Sequence A will be identical to the referenced portion of SEQ ID NO: 1 except that Sequence A may include up to 10 point mutations (such as substitutions with other nucleotides) per each 100 nucleotides of the referenced portion of SEQ ID NO: 1.

Sequence identity for BGT50 and BGT76 (each construct preferably without a coding nucleic acid molecule insert) is preferably set at at least about: 70% identity, at least 80% identity, at least 90% identity, at least 95% identity, at least 96% identity, at least 97% identity, at least 98% identity or, most preferred, at least 99% or 99.5% identity to the sequences of BGT50 or BGT76 provided (such as SEQ ID NO:1–SEQ ID NO:4 or its complementary sequence) or the 5'HS3 promoter, intron 2 and 3' enhancer regions or other regions described in this application, taken in combination or separately). Sequence identity will preferably be calculated with the GCG program from Bioinformatics (University of Wisconsin). Other programs are also available to calculate sequence identity, such as the Clustal W program (preferably using default parameters; Thompson, JD et al., Nucleic Acid Res. 22:4673–4680).

Hybridisation

The invention includes DNA which has a sequence with sufficient identity to a hybrid nucleic acid molecule described in this application to hybridize under stringent hybridization conditions (hybridization techniques are well known in the art). The present invention also includes nucleic acid molecules that hybridize to one or more of the sequences in SEQ ID NO:1–SEQ ID NO:4 or its complementary sequence. Such nucleic acid molecules preferably hybridize under high stringency conditions (see Sambrook et al. Molecular Cloning: A Laboratory Manual, Most Recent Edition, Cold Spring Harbor Laboratory Press, Cold Spring Harbor, N.Y.), High stringency washes have preferably have low salt (preferably about 0.2% SSC) and a temperature of about 50–65 (C.

Regulatory Elements

One skilled in the art would also appreciate that as other regulatory elements in β-globin or nucleic acid molecules to be expressed are identified, these may be used with the hybrid nucleic acid molecules of the invention. Regulatory elements from the β-globin gene in mammals other than humans could be inserted in the hybrid nucleic acid molecule provided that adequate single copy nucleic acid molecule expression still occurs. Regulatory elements from other nucleic acid molecules that are similar to those from the β-globin gene may also be used in the hybrid nucleic acid molecules. These regulatory elements may easily be inserted in hybrid nucleic acid molecules of the invention and the levels of expression measured. For example, regulatory sequences from β-globin genes from other mammals having a high level of sequence identity to the human regulatory elements used in the expression cassettes of the invention may be easily identified by reviewing sequences as they become available in a database, such as Genbank. Suitable sequences preferably have at least about: 70% identity, at least 80% identity, at least 90% identity, at least 95% identity, at least 96% identity, at least 97% identity, at least 98% identity or most preferably have at least 99% or 99.5% identity to the sequence of a regulatory element used in the hybrid nucleic acid molecules of the invention disclosed in this application (or a fragment thereof).

Host Cells

The invention also relates to a host cell (isolated cell in vitro, a cell in vivo, or a cell treated ex vivo and returned to an in vivo site) containing a hybrid nucleic acid molecule of the invention. Cells transfected with a hybrid nucleic acid molecule as a DNA molecule, or transduced with the hybrid nucleic acid molecule as a DNA or RNA virus vector, may be used, or example, in bone marrow or cord blood cell transplants according to techniques known in the art. Examples of the use of transduced bone marrow or cord blood cells in transplants are for ex vivo gene therapy of Adenosine deaminase (ADA) deficiency. Other cells which may be transfected or transduced either ex vivo or in vivo include purified hematopoietic stem cells that are CD34−/CD38−, or CD34+/CD38− in surface marker phenotype, or progenitor cells of the erythroid lineage such as CFU-GEMM, BFU-E and CFU-E, or erythroid cells such as pro-erythroblasts, erythroblasts, or erythrocytes.

Since the DNA regulatory elements used in the hybrid nucleic acid molecules are from human genome, these elements are highly compatible for human gene therapy because the authentic protein factors interacting with these DNA elements are present in targeted cells. These hybrid nucleic acid molecules are erythroid cell-specific and highly efficient. The cell-specificity increases the efficacy and avoids any adverse effects resulting from expression of the therapeutic nucleic acid molecule in non-targeted cells. The high efficiency of gene expression is also critical to minimize the dosage of the therapeutic reagents from gene therapy. Thus, sufficient amounts of the hybrid nucleic acid molecules may be delivered and expressed to confer the phenotype of the expressed polypeptide to the cells (for example, globin activity in erythroid cells).

Pharmaceutical Compositions

The pharmaceutical compositions of this invention used to treat patients having diseases, disorders or abnormal physical states of the cells described in this application could include an acceptable carrier, auxiliary or excipient.

The pharmaceutical compositions can be administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors may also be used.

Dosages to be administered depend on patient needs, on the desired effect and on the chosen route of administration. The expression cassettes may be introduced into the cells or their precursors using ex vivo or in vivo delivery vehicles such as liposomes or DNA or RNA virus vectors. They may also be introduced into these cells using physical techniques such as microinjection or chemical methods such as coprecipitation. The nucleic acid molecules may be introduced into cells of the erythroid lineage, such as erythroid cells or their precursors, such as bone marrow or cord blood cells, purified hematopoietic stem cells that are CD34−/CD38−, or CD34+/CD38−, or progenitor cells of the erythroid lineage such as CFU-GEMM, BFU-E and CFU-E, or erythroid cells such as pro-erythroblasts, erythroblasts, or erythrocytes using these techniques.

The pharmaceutical compositions can be prepared by known methods for the preparation of pharmaceutically acceptable compositions which can be administered to patients, and such that an effective quantity of the hybrid nucleic acid molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as a hybrid nucleic acid molecule, in association with one or more pharmaceutically acceptable vehicles or diluents, and contained in buffered solutions with a suitable pH and isoosmotic with the physiological fluids. The methods of combining the expression cassettes with the vehicles or combining them with diluents is well known to those skilled in the art. The composition could include a targeting agent for the transport of the active compound to specified sites within the erythroid or other cells.

Method of Medical Treatment of Disease

Vectors containing the nucleic acid molecules of the invention may be administered to mammals, preferably humans, in gene therapy using techniques described below. The polypeptides produced from the hybrid nucleic acid molecules may also be administered to mammals, preferably humans.

Gene Therapy

Gene therapy to replace globin expression is useful to modify the development or progression of hemoglobinopathies such as sickle cell anemia and thalassemia. The invention includes compositions and methods for providing a nucleic acid molecule encoding globin to a subject such that expression of the molecule in the cells provides the biological activity of globin and/or phenotype of globin to those cells. The invention also includes compositions and methods for providing gene therapy for treatment of diseases, disorders or abnormal physical states characterized by insufficient globin expression or inadequate levels or activity of globin polypeptide. The compositions and methods specifically deliver high levels of hybrid nucleic acid molecule and high levels of expression in order to provide biological activity of globin and/or pheonotype of globin to cells. One would want at least about 20 and preferably at least about 50% of normal normal wild-type endogenous beta or alpha globin RNA and/or polypeptide levels. HS1, HS2, HS4 and insulator elements, or a combination thereof may be added to the vector to improve the levels of gene expression.

The invention includes methods and compositions for providing a coding nucleotide sequence encoding globin or biologically functional equivalent nucleotide sequence to the cells of an individual such that expression of globin in the cells provides the biological activity or phenotype of globin polypeptide to those cells. Sufficient amounts of the nucleotide sequence are administered and expressed at sufficient levels to provide the biological activity or phenotype of globin polypeptide to the cells. For example, the method can involve a method of delivering and expressing a nucleic acid molecule encoding globin to the cells of an individual having a disease, disorder or abnormal physical state, comprising administering to the individual a vector comprising a hybrid nucleic acid molecule of the invention including a coding nucleic acid molecule encoding globin that can at single copy produces globin. The method also relates to a method for providing an individual having a disease, disorder or abnormal physical state with biologically active globin polypeptide by administering a nucleic acid molecule encoding globin. The method may be performed ex vivo or in vivo. Gene therapy methods and compositions are demonstrated, for example, in U.S. Pat. Nos. 5,869,040, 5,639,642, 5,928,214, 5,911,983, 5,830,880, 5,910,488, 5,854,019, 5,672,344, 5,645,829, 5,741,486, 5,656,465, 5,547,932, 5,529,774, 5,436,146, 5,399,346 and 5,670,488, 5,240,846. The amount of polypeptide will vary with the subject's needs. The optimal dosage of vector may be readily determined using emperical techniques, for example by escalating doses (see U.S. Pat. No. 5,910,488 for an example of escalating doses). As mentioned above, at least about 20 and preferably at least about 50% of normal wild type endogenous beta or alpha globin RNA and/or polypeptide levels is provided to the subject. Other polypeptides may also be delivered using the hybrid nucleic acid molecules of the invention.

Various approaches to gene therapy may be used. The invention includes a process for providing a human with a therapeutic polypeptide including: introducing human cells into a human, said human cells having been treated in vitro or ex vivo to insert therein a vector of the invention at single copy which encodes a globin polypeptide, the human cells expressing in vivo in said human a therapeutically effective amount of said therapeutic polypeptide.

In another embodiment, the invention includes a method for providing biologically active globin polypeptide to the cells of an individual with a hemoglobinopathy, including: introducing an enriched bone marrow hematopoietic progenitor cell population having been treated in vitro or ex vivo to insert therein a DNA molecule at single copy encoding globin polypeptide, the progenitor cell population expressing in said individual biologically active globin polypeptide. In another embodiment, the method of gene therapy includes a method for providing biologically active globin polypeptide to the cells of an individual with a hemoglobinopathy, including:

(a) isolating autologous bone marrow from the individual with the hemoglobinopathy;

(b) enriching the autologous bone marrow for hemapoietic progenitor cells to obtain an enriched hemapoietic progenitor cell population;

(c) transducing the enriched progenitor cell population with the vector of the invention wherein the vector is capable of expressing the globin polypeptide; and (d) transplanting the transduced autologous progenitor cell population into the individual with the hemoglobinopathy so as to provide to the individual biologically active globin polypeptide.

The above methods may be used for medical treatment of any diseases, disorders or abnormal physical states in a cell of an erythroid lineage, preferably including hemoglobinopathy, sickle cell anemia, β-thalassemia and α-thalassemia. The globin is preferably one of the globin genes discussed above, or a derivative.

The method also relates to a method for producing a stock of recombinant virus by producing virus suitable for gene therapy comprising modified DNA encoding globin. This method preferably involves transfecting cells permissive for virus replication (the virus containing modified globin) and collecting the virus produced.

Typically, a male or female is treated with the vector containing the invention (subject age can vary, but subjects include children or adults). An anemic patient patient suffers from tissue hypoxia and anemia symptoms result from cardiovascular and pulmonary responses to the hypoxia. At the time of treatment, for example, a sickle cell anemia patient may have urinary isosthenuria, painful vaso-occlusive crises and leg ulcers. Electrophoesis will show S hemoglobin. A thalassemia patient may have splenomegaly and bony changes on x-ray. A2 and F hemoglobin are often elevated in these patients. The vector containing the invention is preferably administered ex vivo in order to achieve a desired level of polypeptide in the patient. Treatments are repeated as deemed appropriate by a physician to ameliorate the clinical symptoms of disease. Such treatments may be life-long or temporary. Patients report significant reduction in the symptoms described above.

Other hemoglobinopathy, anemias or erythroid diseases, disorders or abnormal physical states that require erythroid specific expression may also be treated. The hybrid nucleic acid molecules are useful for expressing any genes in cells of the erythroid lineage in mammals (including mice or humans), such as genes encoding G6PD or ferrochelatase RNA and/or polypeptides. Marker genes may also be used, such as green fluorescent protein. Derivatives of these polypeptides or globin polypeptides may also be used.

Cotransfection (DNA and marker on separate molecules) may be employed (see eg U.S. Pat. No. 5,928,914 and U.S. Pat. No. 5,817,492). As well, a marker (such as Green Fluorescent Protein marker or a derivative) may be used within the vector itself (preferably a viral vector).

Polypeptide Production and Research Tools

Mammals and cell cultures transfected, transformed or transduced with the hybrid nucleic acid molecules of the invention are useful as research tools. BGT50 and BGT76 are useful as research tools as are other hybrid nucleic acid molecules. Mammals and cell cultures are used in research according to numerous techniques known in the art. For example, one may obtain mice that do not express an α-globin protein and use them in experiments to assess expression of a recombinant α-globin nucleotide sequence under the control of β-globin regulatory elements. In an example of such a procedure, experimental groups of mice are transfected or transduced with vectors containing recombinant α-globin genes (or variants of α-globin or fragments of α-globin) under the control of β-globin regulatory elements to assess the levels of protein produced, its functionality and the phenotype of the mice (for example, physical characteristics of the erythroid cell structure). Some of the changes described above to optimize expression may be omitted if a low level of expression is desired. It would be obvious to one skilled in the art that changes could be made to alter the levels of protein expression.

In another example, a cell line (either an immortalized cell culture or a stem cell culture) is transfected or transduced with a hybrid nucleic acid molecule of the invention (or variants) to measure levels of expression of the nucleic acid molecule and the activity of the nucleic acid molecule. For example, one may obtain mouse or human cell lines or cultures bearing the hybrid nucleic acid molecule of the invention and obtain expression after the transfer of the cells into immunocompromised mice such as NOD/SCID mice.

The hybrid nucleic acid molecules may be used in research to deliver marker genes or antisense RNA to cells.

The invention includes a method for producing a recombinant host cell capable of expressing a nucleic acid molecule of the invention comprising introducing into the host cell a vector of the invention.

The invention also includes a method for expressing a polypeptide in a host cell of the invention including culturing the host cell under conditions suitable for coding nucleic acid molecule expression. The method preferably provides the phenotype of the polypeptide (such as a globin polypeptide or derivative) the cell.

In these methods, the host cell is preferably a cell of the erythroid lineage selected from the group consisting of: an erythroid cell, an erythroid cell precursor, a bone marrow cell, an umbilical cord blood cell, a hematopoietic stem cell that is CD34−/CD38−, or CD34+/CD38−, a progenitor cell of the erythroid lineage, CFU-GEMM, BFU-E, CFU-E, a pro-erythroblast, an erythroblast and an erythrocyte.

Another aspect of the invention is an isolated polypeptide produced from a nucleic acid molecule or vector of the invention according to a method of the invention.

Using Exogenous Agents in Combination with the Hybrid Nucleic Acid Molecule

Cells transfected or transduced with a hybrid nucleic acid molecule may, in appropriate circumstances, be treated with conventional medical treatment of hemoglobinopathies, such as blood transfusions and iron chelators. The appropriate combination of treatments would be apparent to a skilled physician.

IDENTIFICATION OF β-GLOBIN REGULATORY ELEMENTS

Chromatin Opening by the β-globin LCR 5'HS3 Element

The human β-globin LCR is composed of four developmentally stable and erythroid-specific DNaseI hypersensitive sites termed 5'HS 1–4 [2, 11, 12]. The LCR causes high level expression of the β-globin gene locus in cells of the erythroid lineage and each HS seems to provide a unique function for global LCR activation. The LCR activity of each individual HS has been studied extensively in cell culture systems and transgenic mice. Chromatin opening mediated by the human β-globin LCR does not require all four of the HS elements. We have used single-copy transgenic mouse lines to map the LCR chromatin opening activity to a 1.9 kb 5'HS3 fragment when it is linked to the reporter β-globin gene, but expression levels are reduced to about 25% [13]. A transgene construct that contains a dominant chromatin opening activity will escape negative position effects resulting from the neighboring chromatin structure and will express significantly at all single-copy transgene integration sites. In contrast, reproducible expression is not obtained from single-copy transgenes regulated by the 5'HS2 element [14]. DNaseI digestion experiments demonstrated that 5'HS3, but not 5'HS2, could open chromatin at all integration sites tested [13]. In other words, the single-copy transgene assay distinguished between the 5'HS2 classical enhancer element and the 5'HS3 chromatin-opening activity.

Our additional studies used transient day 15.5 embryonic "founder" mice and demonstrated that the minimal 125 bp 5'HS3 core element is not sufficient for single-copy β-globin transgene expression in fetal liver RNA [15]. We also identified an 850 bp 5'HS3 fragment that directs single-copy β-globin transgene expression when part of a larger 3.0 kb LCR [15]. We showed that this 850 bp 5'HS3 element alone confers reproducible single-copy transgene expression on a linked β-globin gene (BGT9 construct, FIG. 1) in transient transgenic mice. However, 5'HS3 is incapable of similarly activating a linked Aγ-globin transgene (BGT26, FIG. 1). These findings show that single-copy transgene expression by 5'HS3 requires cooperation with additional sequences present in the β-globin gene.

Regulatory Elements in the β-globin Gene

Various regulatory elements within the individual β-globin-like genes have been reported and these regulatory elements are responsible for the stage-specific and tissue-specific expression characteristics of the β-globin locus. The β-globin gene in particular has been reported to contain two tissue-specific enhancers, one being an intragenic enhancer in intron 2 (βivs2) [16] and one being 3' to the gene [17]. Furthermore, βivs2 contains a matrix attachment region (MAR) that may influence β-globin gene expression in its natural context. We identified β-globin regulatory elements present within BGT9 that functionally interact with 5'HS3 include the 815 bp promoter, the enhancer or nearby MAR located in βivs2, or the 3' enhancer.

The minimal β-globin promoter maps to a 103 bp fragment that is inducible by the LCR in stable transfection studies and which has been fully footprinted for transcription factor binding sites [18]. LCR activation of multicopy γ-globin transgenes has also been demonstrated to be dependent on the length of the γ-globin promoter [19]. However, the importance of globin promoters in LCR activation has not been systematically evaluated in single-copy transgenic mice. We previously noted that the 265 bp β-globin promoter commonly used in gene therapy vectors does not direct reproducible expression in single-copy transgenic mice regulated by the 3.0 kb LCR cassette [15]. In contrast, the same LCR cassette directed single-copy expression from the 815 bp β-promoter. These findings show that the β-globin promoter has a role in LCR activation.

β-globin enhancers have no role in LCR-mediated induction of the promoter in stable transfection studies [18, 21] and were therefore omitted from β-globin gene therapy vectors [10, 22, 23]. However, deletion of the β-globin 3' enhancer in YAC transgenic mice causes a reduction in β-globin gene expression indicating that the β-globin 3' enhancer influences globin switching [9]. In addition, the human LCR does not reproducibly activate multicopy γ-globin transgene promoters unless a fragment containing the 3' Aγ-globin enhancer [5] or the entire β-globin gene is included [6, 7]. Hence, more recently developed AAV vectors that transfer the Aγ-globin gene include the 3' enhancer [24]. Most recently, it was shown that deletion of the Aγ-globin 3' enhancer in YAC transgenic mice had no effect on transgene expression, throwing some confusion into interpreting these conflicting data. We have shown that reproducible expression from single-copy β-globin transgenes regulated by a 4.0 kb LCR cassette requires a 3' element which includes the β-globin 3' enhancer [8].

β-globin Regulatory Elements Required for Single-copy Transgene Activation by 5'HS3

We fused various β-globin regulatory elements to Aγ-globin coding sequences, and linked these hybrid transgene cassettes to the 850 bp 5'HS3 element. We employed these constructs to fine map the β-globin sequences required for reproducible single-copy transgene expression activity. We showed that the β-globin intron 2 and 3' enhancer are involved in single-copy transgene expression activity mediated by the human β-globin LCR. In addition, we have extended the utility of the β-globin LCR to include expression of the Aγ-globin gene. Such a β/γ-globin hybrid gene is ideally suited for gene therapy of sickle cell anemia because γ-globin protein has better anti-sickling properties than β-globin.

Identifying the Minimal Regulatory Elements to Express a Hybrid Nucleic acid Molecule Definition of the minimal combination of regulatory elements capable of directing expression of the human β-globin gene in single-copy transgenic mice serves the dual purpose of: 1) examining the functional and cooperative interactions of these elements; as well as 2) creating a transgene cassette whose expression levels are well suited for gene therapy purposes. In this study, we define the minimal combination of β-globin gene sequences capable of directing reproducible single-copy transgene expression when linked to 5'HS3. Transgenic mice were used because they provide the most reliable approach to the analysis of mammalian gene expression at the whole organism level. The transgenic mouse model shows that the hybrid nucleic acid molecule functions in other mammals, such as humans.

Our results demonstrate that single-copy expression directed by 5'HS3 is only obtained in the presence of both β-globin intron 2 and 3' enhancer elements. The BGT50 hybrid globin transgene is ideal for gene therapy of hemoglobinopathies because it expresses reproducibly at single-copy and expresses the Aγ-globin gene under β-globin gene regulation. γ-globin protein has better antisickling properties than β-globin [29], and low level expression of γ-globin is known to ameliorate the symptoms of both sickle cell anemia and β-thalassemia.

Requirement for β-globin Intron 2 and 3' Enhancer Elements

The BGT9 construct demonstrates that 850 bp 5'HS3 fragment directs approximately 70% levels of β-globin gene expression at single copy, and confirms that 5'HS3 linked to the β-globin gene is reproducibly expressed at single-copy. The results from the BGT26 transgenic mice establish that the 5'HS3 element cannot reproducibly express the Aγ-globin gene and requires the presence of β-globin gene sequences for activation of single-copy transgenes. A series of β/γ-globin hybrid genes were constructed to define the minimal combination of β-globin gene sequences required for single-copy transgene expression. We conclude from the BGT34 construct that the β-globin promoter is not sufficient for this activity, from the BGT35 construct that the β-globin promoter and β-globin intron 2 are not sufficient, and from the BGT54 construct that the β-globin promoter and β-globin 3' enhancer are not sufficient. In contrast, only the simultaneous presence of the β-globin intron 2 and 3' enhancer in the BGT9, BGT50, and BGT76 constructs was sufficient to confer reproducible single-copy transgene expression directed by 5'HS3. The β-globin promoter is not essential as it can be replaced by the Aγ promoter in the BGT76 construct with little effect on single copy transgene expression. BGT76 includes the Aγ-promoter. HPFH mutations may be made to permit the BGT76 hybrid nucleic acid molecule to be better expressed in adult blood cells. These results show that a functional interaction between 5'HS3, the β-globin intron 2, and 3' enhancer elements is absolutely required for single-copy transgene activation.

Relevance to Gene Therapy of the Hemoglobinopathies

The ability of our hybrid genes to express to high levels at all integration sites and at single copy can be applied to both erythroid-specific transgene expression cassettes in mice and for gene therapy. For example, BGT50 is the first description of Aγ-globin coding sequences controlled by the β-globin regulatory elements, and is well suited for DNA- or viral-mediated gene therapy of both sickle cell anemia and β-thalassemia. Given that BGT50 hybrid transgenes express reproducibly in the fetal livers of transgenic mice, we predict that they will also function when transferred directly into stem cells from cord blood or adult bone marrow, or purified hematopoietic stem cells during a gene therapy protocol. Its 3.9 kb size is small enough for insertion into AAV and retrovirus gene therapy vectors, as well as derivatives of retroviruses (hybrid vectors). The hybrid nucleic acid molecules may also be injected or transfected as a DNA plasmid. However, the MAR element in BGT50 has been reported to be deleterious to retrovirus replication [10, 23]. Viral mediated transfer of the hybrid nucleic acid molecules for gene therapy might be best accomplished with alternative vectors such as Semliki Forest Virus.

Finally, the BGT50 and BGT76 constructs extend the utility of the β-globin LCR in transgenic mice to include reproducible expression of Aγ-globin transgenes. Any nucleic acid molecule could be expressed to high levels in cells of the erythroid lineage by inserting its cDNA or genomic exon/intron sequences (from the ATG site to 3' untranslated sequences) between the NcoI and BamHI sites of BGT50. In this manner, the β-globin intron 2 would function as part of a 3' untranslated region, and the β-globin polyadenylation sites would be used for transcription termination. Such an expression cassette may be extremely useful for directing high level erythroid expression of non-globin transgenes in mice. A candidate nucleic acid molecule of therapeutic use would include the human γ-globin gene and the other genes described in this application.

EXPERIMENTS

In order to determine whether the 850 bp 5'HS3 element alone can direct reproducible single-copy transgene expression when linked to the β-globin gene, we created the BGT9 construct (FIG. 1). The β-globin gene sequences in BGT9 include the 815 bp β-globin promoter, the entire β-globin coding sequences including both introns, and 1.7 kb of 3' sequences including the 3' β-globin enhancer. To determine whether the 850 bp 5'HS3 element requires β-globin gene sequences for single copy transgene expression, we also linked the 850 bp 5'HS3 element to the Aγ-globin gene (BGT26 construct). BGT26 includes the 700 bp Aγ-globin promoter, the entire Aγ-globin coding sequences including both introns, and 2.0 kb of 3' sequences including the 3' Aγ-globin enhancer.

Experiment 1—Generation of Transgenic Mice

These DNA constructs were purified as linear fragments and microinjected into fertilized FVB mouse eggs in order to create transgenic mice. The fetuses derived from these eggs were dissected at embryonic day 15.5 and genomic DNA extracted from head tissue, while the fetal livers were frozen in two halves for future analyses. Positive transient transgenic founder ($F_0$) animals were identified by slot blot hybridization with the 51'HS3 probes, and transgene copy number subsequently deduced by genomic Southern blots after digestion with EcoR1 and BamH1, which we have previously shown can unambiguously identify junction fragments that define single-copy transgenic mice [15]. All founder animals were characterized to determine whether they harboured intact transgenes by Southern blot analysis with multiple diagnostic restriction enzymes and 5'HS3, βivs2, or Aγ-globin 3' probes (data not shown). Finally, the proportion of transgenic cells in the fetal liver was compared to a bred line control by Southern blot analysis. DNA derived from one half of the frozen fetal livers was digested with Acc1 (BGT9) or Pst1 (Aγ-globin transgenes) and the transgene detected by the 5'HS3, βivs2, or βpromoter probes (data not shown). Animals containing a single non-intact transgene or highly mosaic animals (<10%) were excluded from this study.

Experiment 2—Requirement for β-globin Gene Sequences

Figure 2:
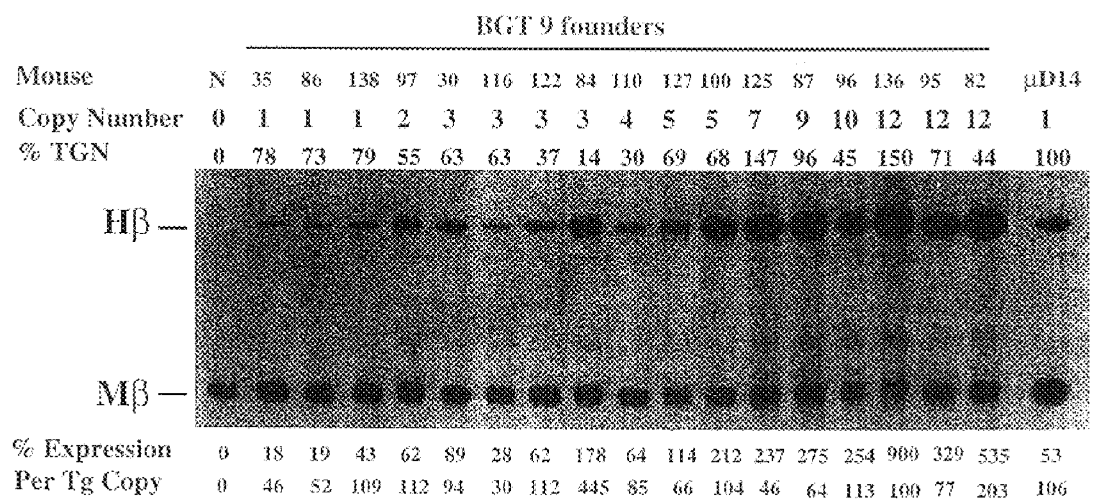

To determine the effect of these transgene constructs on expression levels, RNA was extracted from frozen transgenic fetal livers for S1 nuclease protection assays. For the BGT9 construct, expression was analyzed using Hβ and Mβ probes (FIG. 2). As a standard sample for quantitation of Huβ RNA levels, we included fetal liver RNA from μD14 transgenic mice that express to approximately 100% levels. The BGT9 construct expresses significant levels of human β-globin mRNA in all 17 transgenic mice. Expression from three single-copy BGT9 mice ranges from 46–109% of the Mβ RNA, demonstrating that the 850 bp 5'HS3 element directs reproducible single-copy transgene expression when linked to the entire β-globin gene. In addition, the BGT9 construct appears to express to a higher level at single copy than the previously described 26% levels from the 1.9 kb 5'HS3 element [13].

Figure 3:
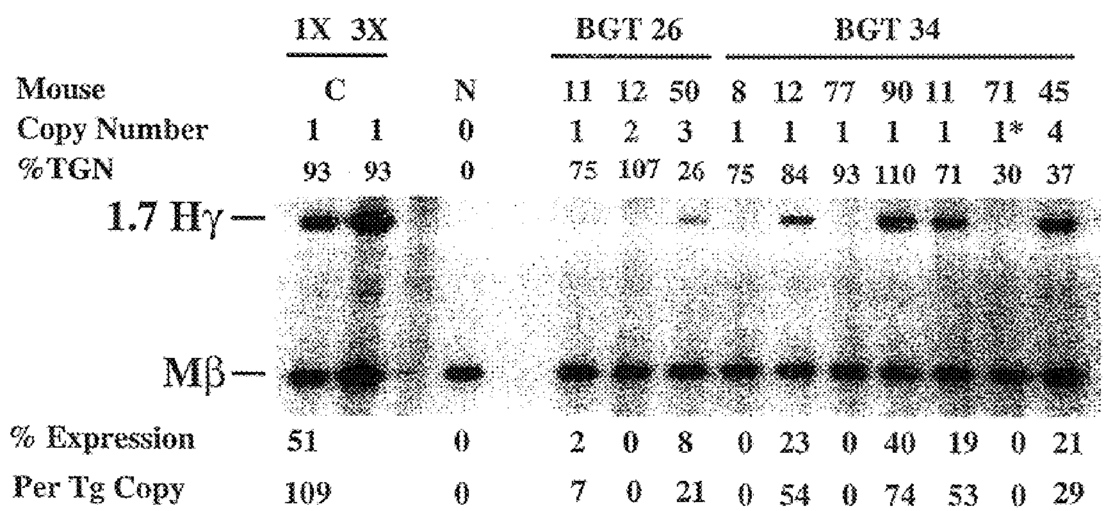

Similar expression analysis was performed on the BGT26 transgene using the Hγ and Mβ probes (FIG. 3). As a standard RNA sample for all the Hγ S1 nuclease experiments, we included BGT50–48 RNA (labelled C in all figures). BGT50–48 is equivalent to the highest expressing single-copy BGT9 mouse, in that it contains one intact copy of the BGT50 construct (described later) and expresses γ-globin at 109% the level of Mβ (mean value from 8 experiments). Analysis of BGT26 transgenic mice shows very low levels of Aγ-globin mRNA in 2 mice and an undetectable level in the third animal. These data demonstrate that 5'HS3 cannot direct reproducible transgene expression on a linked Aγ-globin gene and suggests that 5'HS3 must functionally interact with β-globin gene sequences in order to reproducibly activate single-copy transgenes.

Experiment 3 - Design of Novel 5'HS3 β/γ-globin Hybrid Transgenes

To identify the β-globin gene sequences required to obtain reproducible single-copy transgene expression, we created several novel hybrid globin genes linked to the 5'HS3 element (FIG. 1). BGT34 contains 5'HS3 linked to the β-globin 815 bp promoter and the Aγ-globin coding sequences terminating 375 bp downstream of exon 3. This construct does not contain the Aγ-globin 3' enhancer, and the Aγ-globin intron 2 has no known enhancer activity. Expression by this construct would indicate that the β-globin promoter is sufficient for single-copy transgene by 5'HS3.

BGT35 is essentially the same as BGT34 but with a replacement of the Aγ-globin intron 2 sequences with the βivs2. This adds the β-globin intron 2 enhancer and MAR to the BGT34 construct, but also alters three amino acids in the Aγ-globin coding sequences to their equivalents in the β-globin gene (K104R, T112K, I116H). These changes do not alter amino-acids known to be important for anti-sickling effects [29]. Expression by BGT35 would indicate that both the β-globin promoter and intron 2 are sufficient for single-copy transgene activation by 5'HS3.

BGT54 is essentially the same as BGT34 but with the addition of the 200 bp β-globin 3' enhancer 375 bp downstream of the Aγ-globin coding sequences. Expression by BGT54 would indicate that both the β-globin promoter and β-globin 3' enhancer are sufficient for single-copy transgene activation by 5'HS3. BGT50 is essentially the same as BGT35 but with the β-globin 3' enhancer inserted 375 bp downstream of the Aγ-globin exon 3. This construct also contains the three amino acid alteration in the Aγ-globin coding sequences. Expression by BGT50 would indicate that the β-globin promoter, β-globin intron 2 and β-globin 3' enhancer are sufficient for single-copy transgene activation by 5'HS3.

Experiment 4—Expression of 5'HS3 β/γ-globin Hybrid Transgenes

Expression from each of the 5'HS3 β/γ-globin constructs was assayed in transgenic mice by S1 nuclease protection analysis in the fetal liver of 15.5 day transient transgenic mice as above. Of 7 BGT34 transgenic mice that include the 815 bp β-globin promoter (FIG. 3), 5 animals contained a single-copy of the transgene and one animal (34–71) contained one intact copy and a partial transgene (indicated by the asterisk). Only 3/5 single-copy animals and one four copy animal (34–45) expressed detectable levels of human Aγ-globin mRNA on a per copy basis. This finding demonstrates that the β-globin promoter is not sufficient to rescue reproducible expression from single-copy transgenes that lack a 3' enhancer element.

Figure 4:
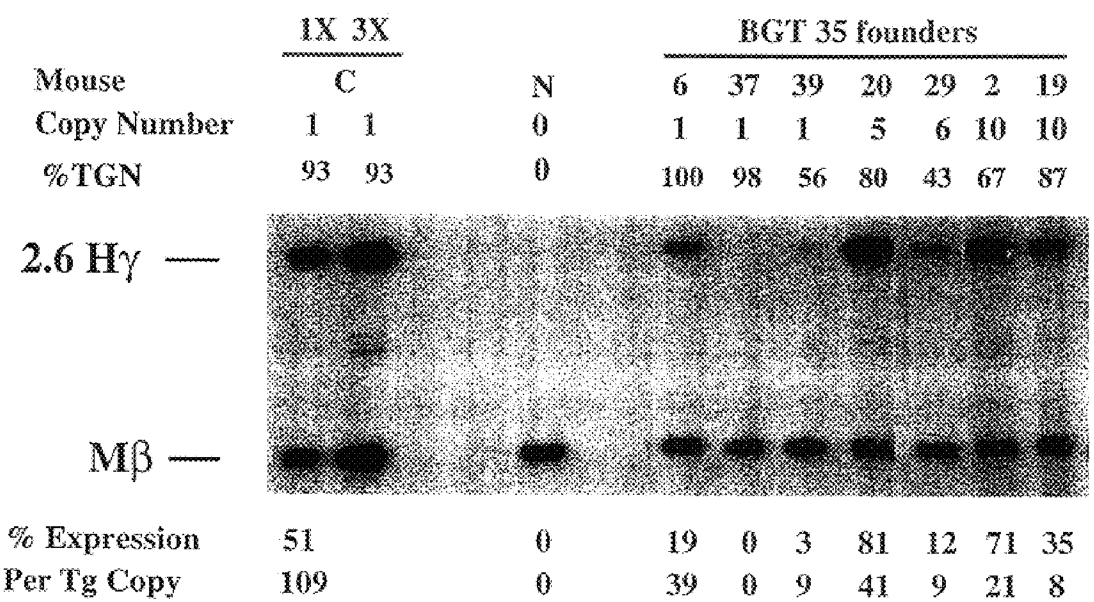
Figure 5:
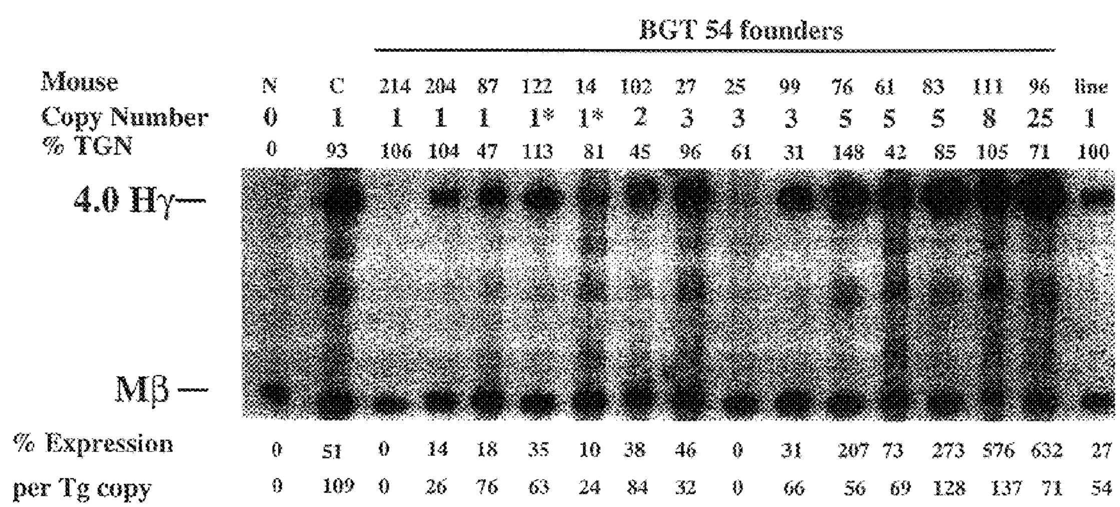

Other candidate β-globin sequences that may functionally interact with 5'HS3 include the enhancers in βivs2 and 3' of the gene. Therefore, we analyzed 5'HS3 Aγ-globin transgenes containing the 815 bp β-globin promoter and either βivs2 (BGT 35; FIG. 1) or the 3' enhancer (BGT 54; FIG. 1) or both (BGT 50; FIG. 1). 3 out of 7 BGT35 animals contained one single intact transgene (FIG. 4). Of these single-copy mice, low or undetectable Aγ-globin mRNA levels were observed in 2 animals. These data show that the β-globin promoter and β-globin intron 2 are also not sufficient for reproducible transgene expression directed by 5'HS3. We generated six single-copy BGT54 animals (FIG. 5), two of which contained one intact transgene and a partial transgene (indicated by the asterisk). The "line" sample represents a single-copy bred line where RNA expression was assayed in the adult blood. BGT54 expresses significant levels of Aγ-globin mRNA in 5/6 single-copy animals including the adult blood sample of the BGT54 transgenic line. However, one single-copy and a three copy animal express undetectable levels of Aγ-globin mRNA. This finding demonstrates that the β-globin promoter and β-globin 3' enhancer are not sufficient for reproducible transgene expression.

Figure 6:
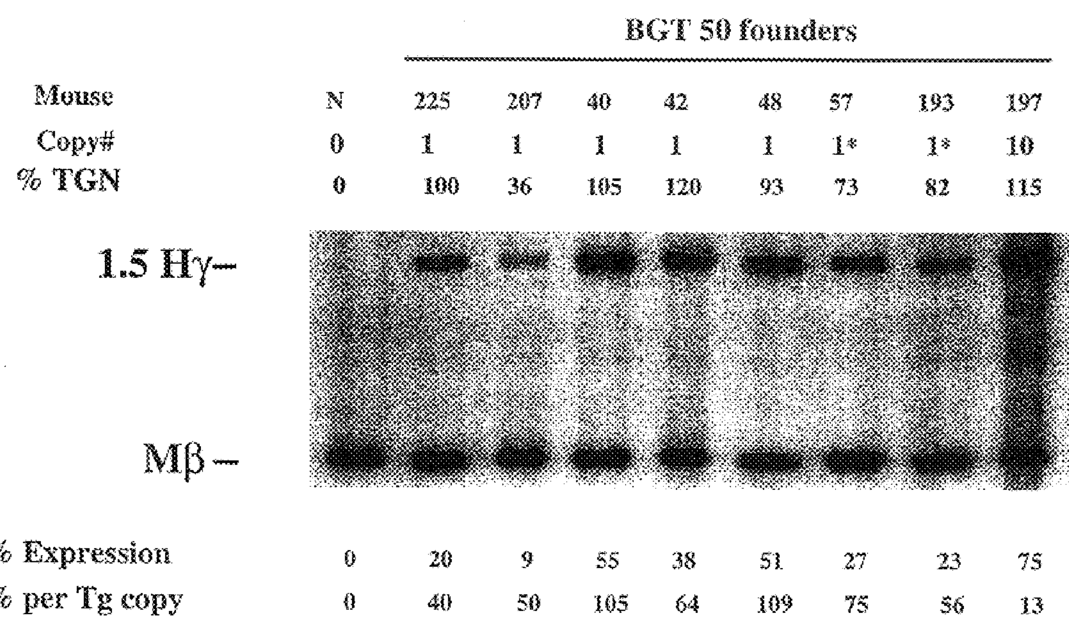

Finally, the BGT50 construct was tested in single-copy transgenic mice and significant expression was detected in all eight transgenic mice (FIG. 6). Seven single-copy animals were generated, two of which contained a partial transgene along with an intact transgene (indicated by the asterisk). One animal (50–225) is a single-copy bred line sample where RNA was assayed in the fetal liver. The average expression of single-copy transgenes is 71 % of Mβ levels and ranges from 40%–109%. Since only BGT50 was expressed in all single-copy kansgenic mice and, therefore, irrespective of the integration site, we conclude that reproducible single-copy transgene activation by 5'HS3 on the β-globin promoter requires a functional interaction with both βivs2 and the 3' enhancer.

Experiment 5—Requirement for the β-globin Promoter

In order to determine whether the β-globin promoter is required, or that βivs2 and β-globin 3' enhancer are themselves sufficient for single-copy transgene activation by 5'HS3, we created the BGT76 construct (FIG. 1). BGT76 is essentially the same as BGT50 with the replacement of the 815 bp β-globin promoter for the 700 bp Aγ-globin promoter. Expression by BGT76 would indicate that the functional interaction between 5'HS3 and these β-globin elements is not specific for activation of the β-globin promoter.

Figure 7:
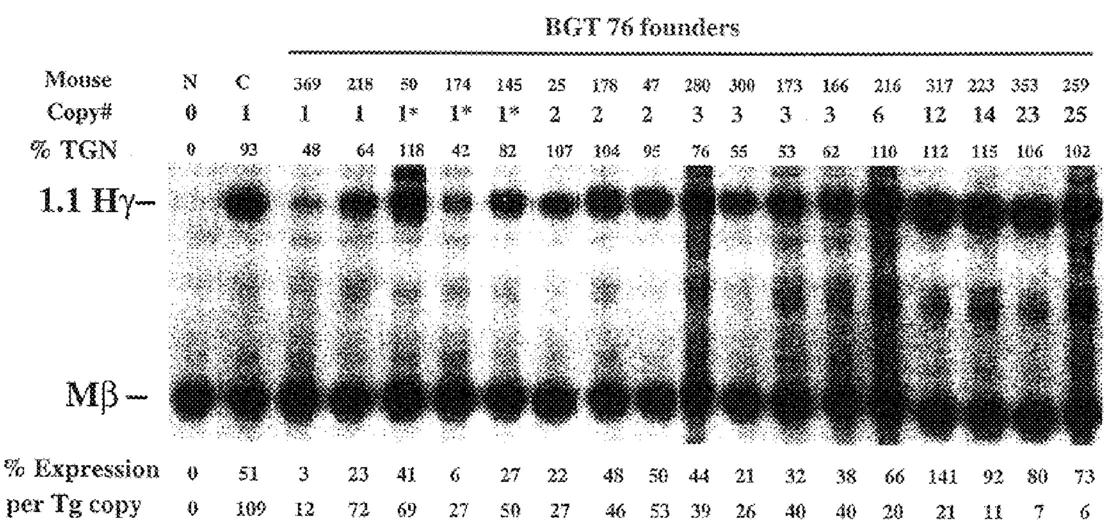

Expression from BGT76 was assayed in transgenic mice by S1 nuclease protection analysis in the fetal liver of 15.5 day transient transgenic mice as above. 17 of 17 BGT76 transgenic mice expressed detectable levels of human Aγ-globin mRNA (FIG. 7). Five single-copy animals were generated, three of which also contained a partial transgene (indicated by the asterisk). These single-copy transgenic mice expressed a mean 46% Mβ levels ranging from 12%–72%. This finding demonstrates that the activation of single-copy transgenes is not dependent on the presence of the β-globin promoter. We conclude that the Aγ-globin promoter can also be activated by a functional interaction between 5'HS3, β-globin intron 2 and 3' elements.

MATERIALS AND METHODS

Plasmid Construction

Transgene constructs were derived from the plasmids pGSE1758 [28], pBGT14 [15], p141 [23], and pAγ-globin (provided by S. Philipsen). pGSE1758 contains a polylinker 5' of the 4.2 kb Hβa1-EcoRV β-globin gene fragment regulated by the 815 bp promoter. pBGT14 contains a 3.0 kb LCR cassette and the 4.2 kb Hβa1-EcoRV β-globin gene fragment regulated by the 815 bp promoter [15]. The 3.0 kb LCR contains the 1.15 kb Stu1-Spe1 fragment of 5'HS4, the 0.85 kb Sac1-PvuII fragment of 5'HS3, and the 0.95 kb Sma1-Stu1 fragment of 5'HS2. p141 contains a SnaBI-PstI β-globin gene fragment which includes a 372 bp RsaI-RsaI deletion in intron 2.

BGT9 was constructed by inserting the 850 bp Sac1-PvuII fragment of 5'HS3 into the XhoI site of pGSE1758 using XhoI linkers. The 5.0 kb transgene including the entire β-globin gene was purified as an EcoRV fragment.

BGT26 replaces all the β-globin gene sequences in BGT9 between the Sal1-XbaI sites with the 4.3 kb BspHI fragment of Aγ-globin by blunt end ligation. This includes the Aγ-globin 700 bp promoter and 3' enhancer. The 5.2 kb transgene was purified as an EcoRV fragment.

BGT34 inserts the 1.9 kb NcoI-HindIII fragment from Aγ-globin into the NcoI-EcoRV sites of BGT9 using an NheI linker at the incompatible HindIII and EcoRI overhangs. The Aγ-globin sequences extend from the ATG translation start site located at the NcoI site used for subcloning, to 375 bp 3' of exon 3 including the polyA site but not the Aγ-globin 3' enhancer. The end result is that BGT34 contains the 815 bp β-globin promoter controlling the entire Aγ-globin coding sequences and both introns. The 3.7 kb transgene was purified as an EcoRV-NheI fragment.

BGT35 inserts the β-globin intron 2 sequences as a BamHI-EcoRI fragment into the compatible BamHI-EcoRI sites of BGT34. These changes also replace 4 Aγ-globin codons (101–104) with β-globin exon 2 sequences, and 16 Aγ-globin codons (105–119) with β-globin exon 3 sequences. Of these 20 β-globin codons, 17 encode the same amino-acid as Aγ-globin. The three altered codons are described in the text. The end result is that BGT35 contains the 815 bp β-globin promoter and the β-globin intron 2 sequences controlling the Aγ-globin coding sequences. The 3.7 kb transgene was purified as an EcoRV-NheI fragment.

BGT50 contains a polylinker at the NheI site of BGT35 that adds EcoRV, AgeI, and ClaI sites 3' of the hybrid globin gene. The 260 bp PstI fragment containing the β-globin 3' enhancer was cloned into the NheI site using linkers. The end result is that BGT50 contains the 815 bp β-globin promoter, the βivs2, and the β-globin 3' enhancer controlling the Aγ-globin coding sequences. The 3.9 kb transgene was purified as a ClaI fragment.

BGT54 contains the 3.0 kb ClaI-EcoRI fragment of BGT34 linked to the 850 bp EcoRI-ClaI fragment of BGT50. The end result is that BGT54 contains the 815 bp β-globin promoter and the β-globin 3' enhancer controlling the entire Aγ-globin coding sequences and both introns. The 3.9 kb transgene was purified as a ClaI fragment.

BGT76 contains the 2.1 kb ClaI-BamHI fragment of BGT26 linked to the 1.7 kb BamHI-ClaI fragment of BGT50. The end result is that BGT76 contains the 700 bp Aγ-globin promoter, the βivs2, and β-globin 3' enhancer controlling the Aγ-globin coding sequences. The 3.8 kb transgene was purified as a ClaI fragment.

Generation of Transgenic Mice

Transgene DNA was prepared using Plasmid Maxi Kits (Qiagen). Transgene fragments were liberated from their plasmid backbones by digestion with the stated restriction enzymes. DNA fragments were recovered from 0.7% TAE agarose gel slices using GeneClean II or GeneClean Spin Column Kits (Bio101) and Elutip-d columns (Schleicher and Schuell), and resuspended in injection buffer (10 mM Tris-HCl pH 7.5, 0.2 mM EDTA). DNA concentration was determined by comparison with DNA standards run on agarose gels, and the injection fragment was diluted to 0.5–1 ng/μl in injection buffer. The diluted DNA was prespun for 20 minutes and aliquots removed for microinjection into fertilized FVB mouse eggs. Injected eggs were transferred into recipient CD1 female animals. 15.5 days post-injection, fetal mice were dissected and DNA extracted from head tissue while the fetal livers were saved frozen in two halves for future analysis. Head DNA was extracted by Proteinase K digestion overnight, a single phenol/chloroform extraction and isopropanol precipitation. Transient transgenic fetuses were identified by slot blot hybridization with the 5'HS3 probe using standard procedures.

DNA Analysis

Southern transfer and hybridization were by standard procedures. Cop-number determination was performed using a Molecular Dynamics PhosphorImager. Single-copy animals showed a single random sized end-fragment in BamH1 and EcoR1 digests hybridized with the 5'HS3, βivs2 or Aγ-globin 3' probes. With multicopy animals, the intensity of the end-fragment was defined as one transgene copy, and was used to calculate the copy number of the multicopy junction-fragment in the same lane. The intactness of the transgene in the DNA sample was verified by Southern blot analysis using two sets of digests, one for 5' intactness and one for 3' intactness, appropriate for each construct. The resulting fragments were hybridized to either βivs2, 5'HS3, or Aγ-globin 3' probes. Mice that were mosaic for the transgene were excluded from the study by demonstration of insignificant transgene contribution to the fetal liver by Southern blot analysis of fetal liver DNA.

RNA Analysis

Fetal liver (embryonic day 15.5) RNA was extracted using Trizol Reagent (Gibco BRL), 1 μg was hybridized to [γATP]-labeled double-stranded 5'DNA probe for human β-globin detection or a [αdATP]-labeled double-stranded 3' DNA probe for human Aγ-globin detection. A [γATP]-labeled double-stranded 5'DNA probe was used for mouse β-globin major detection used as a loading control. RNA/DNA hybrids were subsequently digested with 75 U S1 nuclease (Boehringer Mannheim) and run on a 6% sequencing gel as described [16]. Probe excess was demonstrated by including a sample containing 3 μg fetal liver RNA. Specific activities of human β-globin (Hβ) or human Aγ-globin (Hγ) relative to the mouse ,major (Mβ) probe is described for each S1 nuclease experiment in the corresponding figure legend. The protected 170 nt Hγ, 160 nt Hβ, and 95 nt Mβ bands were quantified on a Molecular Dynamics PhosphorImager and the % expression levels calculated according to the formula (Hβ or γ/Mβ)×100% and corrected for specific activity differences between the probe preparations. % Expression per transgene copy was calculated as (2 Mβ genes/number Hβ or γ transgenes)×(% expression)/(% transgenicity)×100%.

The present invention has been described in detail and with particular reference to the preferred embodiments; however, it will be understood by one having ordinary skill in the art that changes can be made thereto without departing from the spirit and scope of the invention.

All publications, patents and patent applications, including Canadian application no. 2,246,005, are incorporated by reference in their entirety to the same extent as if each individual publication, patent or patent application was specifically and individually indicated to be incorporated by reference in its entirety.

REFERENCES

1. Miller, A. D., Human gene therapy comes of age. Nature, 1992. 357(6378): p. 455–60.
2. Grosveld, F., et al., Position-independent, high-level expression of the human beta-globin gene in transgenic mice. Cell, 1987. 51(6): p. 975–85.
3. Tewari, R., et al., The human beta-globin locus control region confers an early embryonic erythroid-specific expression pattern to a basic promoter driving the bacterial lacZ gene. Development, 1996. 122(12): p. 3991–9.
4. Guy, L.G., et al., The beta-globin locus control region enhances transcription of but does not confer position-independent expression onto the lacZ gene in transgenic mice. EMBO Journal, 1996. 15(14): p. 3713–21.
5. Stamatoyannopoulos, J. A., C. H. Clegg, and Q. Li, Sheltering of gamma-globin expression from position effects requires both an upstream locus control region and a regulatory element 3' to the A gamma-globin gene. Molecular & Cellular Biology, 1997. 17(1): p. 240–7.
6. Roberts, N. A., et al., Globin gene switching in transgenic mice carrying HS2-globin gene constructs. Blood, 1997. 89(2): p. 713–23.
7. Li, Q. and J. A. Stamatoyannopoulos, Position independence and proper developmental control of gamma-globin gene expression require both a 5' locus control region and a downstream sequence element. Molecular & Cellular Biology, 1994. 14(9): p. 6087–96.
8. Pasceri, P., et al., Full activity from human beta-globin locus control region transgenes requires 5'HS1, distal beta-globin promoter, and 3'beta-globin sequences. Blood, 1998. 92(2): p. 653–63.
9. Liu, Q., J. Bungert, and J. D. Engel, Mutation of gene-proximal regulatory elements disrupts human epsilon-, gamma-, and beta-globin expression in yeast artificial chromosome transgenic mice. Proceedings of the National Academy of Sciences of the United States of America, 1997. 94(1): p. 169–74.
10. Sadelain, M., et al., Generation of a high-titer retroviral vector capable of expressing high levels of the human beta-globin gene. Proceedings of the National Academy of Sciences of the United States of America, 1995. 92(15): p. 6728–32.
11. Tuan, D., et al., The "beta-like-globin" gene domain in human erythroid cells. Proceedings of the National Academy of Sciences of the United States of America, 1985. 82(19): p. 6384–8.
12. Forrester, W. C., et al., A developmentally stable chromatin structure in the human beta-globin gene cluster. Proceedings of the National Academy of Sciences of the United States of America, 1986. 83(5): p. 1359–63.
13. Ellis, J., et al., A dominant chromatin-opening activity in 5' hypersensitive site 3 of the human beta-globin locus control region. EMBO Journal, 1996. 15(3): p. 562–8.
14. Ellis, J., et al., Synthetic human beta-globin 5'HS2 constructs function as locus control regions only in multicopy transgene concatamers. EMBO Journal, 1993.,12 (1): p. 127–34.
15. Ellis, J., et al., Evaluation of beta-globin gene therapy constructs in single copy transgenic mice. Nucleic Acids Research, 1997. 25(6): p. 1296–302.
16. Antoniou, M., et al., The human beta-globin gene contains multiple regulatory regions: identification of one promoter and two downstream enhancers. EMBO Journal, 1988. 7(2): p. 377–84.
17. Wall, L., E. deBoer, and F. Grosveld, The human beta-globin gene 3' enhancer contains multiple binding sites for an erythroid-specific protein. Genes & Development, 1988. 2(9): p. 1089–100.
18. Antoniou, M. and F. Grosveld, beta-globin dominant control region interacts differently with distal and proximal promoter elements. Genes & Development, 1990. 4(6): p. 1007–13.
19. Stamatoyannopoulos, G., et al., Developmental regulation of human gamma-globin genes in transgenic mice. Molecular & Cellular Biology, 1993. 13(12): p. 7636–44.

20. Behringer, R. R., et al, Two 3' sequences direct adult erythroid-specific expression of human beta-globin genes in transgenic mice. Proceedings of the National Academy of Sciences of the United States of America, 1987. 84(20): p. 7056–60.

21. Collis, P., M. Antoniou, and F. Grosveld, Definition of the minimal requirements within the human beta-globin gene and the dominant control region for high level expression. EMBO Journal, 1990. 9(1): p. 233–40.

22. Einerhand, M. P., et al., Regulated high-level human beta-globin gene expression in erythroid cells following recombinant adeno-associated virus-mediated gene transfer. Gene Therapy, 1995. 2(5): p. 336–43.

23. Leboulch, P., et al., Mutagenesis of retroviral vectors transducing human beta-globin gene and beta-globin locus control region derivatives results in stable transmission of an active transcriptional structure. EMBO Journal, 1994. 13(13): p. 3065–76.

24. Hargrove, P. W., et al., High-level globin gene expression mediated by a recombinant adeno-associated virus genome that contains the 3'gamma globin gene regulatory element and integrates as tandem copies in erythroid cells. Blood, 1997. 89(6): p. 2167–75.

25. Huber, M. C., et al., The developmental activation of the chicken lysozyme locus in transgenic mice requires the interaction of a subset of enhancer elements with the promoter. Nucleic Acids Research, 1997. 25(15): p. 2992–3000.

26. Mason, M. M., et al., Expression of the chicken beta-globin gene cluster in mice: correct developmental expression and distributed control. Molecular & Cellular Biology, 1995. 15(1): p. 407–14.

27. Reitman, M., et al., An enhancer/locus control region is not sufficient to open chromatin. Molecular & Cellular Biology, 1993. 13(7): p. 3990–8.

28. Talbot, D., et al., A dominant control region from the human beta-globin locus conferring integration site-independent gene expression. Nature, 1989. 338(6213): p. 352–5.

29. Takekoshi, K. J., et al., Retroviral transfer of a human beta-globin/delta-globin hybrid gene linked to beta locus control region hypersensitive site 2 aimed at the gene therapy of sickle cell disease. Proceedings of the National Academy of Sciences of the United States of America, 1995. 92(7): p. 3014–8.

We claim:

1. A hybrid nucleic acid molecule that when integrated into the genome at single gene copy produces an RNA encoding a polypeptide in a targeted mammalian cell of the erythroid lineage, comprising: i) globin nucleic acid regulatory elements comprising a) a β-globin 5'HS3, b) a β-globin promoter or an Aγ-globin promoter, c) a β-globin intron 2, d) a β-globin 3' enhancer; and ii) a β-globin coding nucleic acid molecule operatively associated with the regulatory elements and capable of expression in the cell.

2. The hybrid nucleic acid molecule of claim 1, wherein the mammalian cell is a human cell.

3. A vector comprising the nucleic acid molecule of claim 1.

4. A composition comprising the vector of claim 3.

5. An isolated host cell comprising the vector of claim 3.

6. The host cell of claim 5, wherein the host cell is a cell of the erythroid lineage selected from the group consisting of: an erythroid cell, an erythroid cell precursor, a bone marrow cell, an umbilical cord blood cell, a hematopoietic stem cell, a hematopoietic stem cell that is CD34−/CD38−, or CD34+/CD38−, a progenitor cell of the erythroid lineage, CFU-GEMM, BFU-E, CFU-E, a pro-erythroblast an erythroblast and an erythrocyte.

7. A method for expressing a nucleic acid molecule in a mammalian cell of the erythroid lineage in vitro, comprising a) administering to the cell an effective amount of the hybrid nucleic acid molecule of claim 1 so that the hybrid nucleic acid molecule is inserted into the genome at single gene copy and b) expressing the nucleic acid molecule to produce a γ-globin RNA and its encoded polypeptide.

8. A method for producing γ-globin polypeptide in a mammalian cell of the erythroid lineage in vitro, comprising a) administering to the cell an effective amount of the hybrid nucleic acid molecule of claim 1 so that the hybrid nucleic acid molecule is inserted into the genome at single gene copy and b) expressing the nucleic acid molecule to produce γ-globin RNA and its encoded polypeptide.

9. The hybrid nucleic acid molecule of claim 1, comprising all or part of a nucleic acid molecule selected from the group consisting of: a) SEQ ID NO:1, SEQ ID NO:2, SEQ ID NO:3, and SEQ ID NO:4, or complements thereof.

10. The hybrid nucleic acid molecule of claim 1, wherein the molecule hybridizes to a nucleic acid molecule of any one of SEQ ID NO:1 to SEQ ID NO:4, or a complement thereof under high stringency hybridization conditions comprising 0.2% SSC and a temperature of 65° C., the nucleic acid molecule producing an RNA encoding a polypeptide in a targeted mammalian cell of the erythroid lineage when the nucleic acid molecule is integrated into the genome at single gene copy.

11. The hybrid nucleic acid molecule of claim 1, wherein the β-globin 5'HS3 comprises all or part of nucleotide nos. 28–882 of SEQ ID NO:2, the β-globin promoter comprises all or part of nucleotide nos. 903–1771 SEQ ID NO:2, the β-globin intron 2 comprises all or part of nucleotide nos. 2191–3108 of SEQ ID NO:2 and the β-globin 3' enhancer comprises all or part of nucleotide nos. 3655–3912 of SEQ ID NO:2.

12. The hybrid nucleic acid molecule of claim 1, wherein the β-globin 5'HS3 comprises all or part of nucleotide nos. 23–877 of SEQ ID NO:4, the Aγ-globin promoter comprises all or part of nucleotide nos. 896–1655 SEQ ID NO:4, the β-globin intron 2 comprises all or part of nucleotide nos. 2075–2992 of SEQ ID NO:4 and the β-globin 3' enhancer comprises all or part of nucleotide nos. 3539–3796 of SEQ ID NO:4.

13. A nucleic acid molecule having at least about 97% identity with the nucleic acid molecule of any one of SEQ ID NO:1 to SEQ ID NO:4, or a complement thereof, the nucleic acid molecule producing an RNA encoding a polypeptide in a targeted mammalian cell of the erythroid lineage when the nucleic acid molecule is integrated into the genome at single gene copy, wherein the nucleic acid molecule comprises globin nucleic acid regulatory elements: (a) a β-globin 5'HS3; (b) a β-globin intron 2 and (c) a β-globin 3'enhancer.

14. The nucleic acid molecule of claim 13 which further comprises a β-globin promoter or an Aγ-globin promoter.

15. A hybrid nucleic acid molecule that when integrated into the genome at single gene copy produces an RNA encoding a polypeptide in a targeted mammalian cell of the erythroid lineage, comprising globin regulatory elements having at least 90% sequence identity to the globin regulatory elements selected from the group consisting of a β-globin promoter comprising nucleotide nos. 903–1771 of SEQ ID NO:2 and Aγ-globin promoter comprising nucleotide nos. 896–1655 of SEQ ID NO:4, and having at least 97% sequence identity to globin nucleic acid regulatory elements: (a) a β-globin 5'HS3 comprising 28–882 of SEQ ID NO:2 or 23–887 of SEQ ID NO:4; (b) a β-globin intron 2 comprising nucleotide nos. 2191–3108 of SEQ ID NO:2 or 2075–2002 of SEQ ID NO:4 and (c) a β-globin 3' enhancer comprising nucleotide nos. 3655–3912 of SEQ ID NO:2 or 3539–3796 of SEQ ID NO:4, wherein the nucleic acid molecule comprises the following globin nucleic acid regulatory elements:(a) a β-globin 5'HS3; (b) a β-globin intron 2; (c) a β-globin 3' enhancer; (d) a promoter selected from the group consisting of a β-globin promoter and a Aγ-globin promoter.

16. A hybrid nucleic acid molecule that when integrated into the genome at single gene copy produces an RNA encoding a polypeptide a targeted mammalian cell of the erythroid lineage, comprising globin regulatory elements having at least 95% sequence identity to the globin regulatory elements selected from the group consisting of a (-globin promoter comprising nucleotide nose 903–1771 of SEQ ID NO:2 and Aγ-globin promoter comprising nucleotide nos. 896–1655 of SEQ ID NO:4, and having at least 97% sequence identity to β-globin nucleic acid regulatory elements: (a) a 5'HS3 comprising 28–882 of SEQ ID NO:2 or 23–887 of SEQ ID NO:4; (b) a β-globin intron 2 comprising nucleotide nos. 2191–3108 of SEQ ID NO:2 or 2075–2002 of SEQ ID NO:4 and (c) a β-globin 3' enhancer comprising nucleotide nos. 3655–3912 of SEQ ID NO:2 or 3539–3796 of SEQ ID NO:4, wherein the nucleic acid molecule comprises the following globin nucleic acid regulatory elements: (a) a β-globin 5'HS3; (b) a β-globin intron 2; (c) a β-globin 3' enhancer; (d) a promoter selected from the group consisting of a β-globin promoter and a Aγ-globin promoter.

* * * * *

SEQUENCE LISTING

<160> NUMBER OF SEQ ID NOS: 4

<210> SEQ ID NO 1
<211> LENGTH: 3496
<212> TYPE: DNA
<213> ORGANISM: Homo sapiens

<400> SEQUENCE: 1
cgatgaagct tcctcgaggc agaagagtca agcatttgcc taaggtcgga catgtcagag 60
gcagtgccag acctatgtga gactctgcag ctactgctca tgggccctgt gctgcactga 120
tgaggaggat cagatggatg gggcaatgaa gcaaaggaat cattctgtgg ataaaggaga 180
cagccatgaa gaagtctatg actgtaaatt tgggagcagg agtctctaag gacttggatt 240
tcaaggaatt ttgactcagc aaacacaaga ccctcacggt gactttgcga gctggtgtgc 300
cagatgtgtc tatcagaggt tccagggagg gtggggtggg gtcagggctg gccaccagct 360
atcagggccc agatgggtta taggctggca ggctcagata ggtggttagg tcaggttggt 420
ggtgctgggt ggagtccatg actcccagga gccaggagag atagaccatg agtagagggc 480
agacatggga aaggtggggg aggcacagca tagcagcatt tttcattcta ctactacatg 540
ggactgctcc cctataccccc cagctagggg caagtgcctt gactcctatg ttttcaggat 600
catcatctat aaagtaagag taataattgt gtctatctca tagggttatt atgaggatca 660
aaggagatgc acactctctg gaccagtggc ctaacagttc aggacagagc tatgggcttc 720
ctatgtatgg gtcagtggtc tcaatgtagc aggcaagttc cagaagatag catcaaccac 780
tgttagagat atactgccag tctcagagcc tgatgttaat ttagcaatgg gctgggaccc 840
tcctccagta gaaccttcta accagcctcg agggactagt cggtaccgtc gacaacctcc 900
tatttgacac cactgattac cccattgata gtcacacttt gggttgtaag tgactttttta 960 tttatttgta tttttgactg cattaagagg tctctagttt tttatctctt gtttcccaaa 1020
acctaataag taactaatgc acagagcaca ttgatttgta tttattctat ttttagacat 1080
aatttattag catgcatgag caaattaaga aaaacaacaa caaatgaatg catatatatg 1140

-continued

```
tatatgtatg tgtgtatata tacacatata tatatatatt ttttttcttt tcttaccaga   1200
aggttttaat ccaaataagg agaagatatg cttagaactg aggtagagtt ttcatccatt   1260
ctgtcctgta agtattttgc atattctgga gacgcaggaa gagatccatc tacatatccc   1320
aaagctgaat tatggtagac aaagctcttc cacttttagt gcatcaattt cttatttgtg   1380
taataagaaa attgggaaaa cgatcttcaa tatgcttacc aagctgtgat tccaaatatt   1440
acgtaaatac acttgcaaag gaggatgttt ttagtagcaa tttgtactga tggtatgggg   1500
ccaagagata tatcttagag ggagggctga gggtttgaag tccaactcct aagccagtgc   1560
cagaagagcc aaggacaggt acggctgtca tcacttagac ctcaccctgt ggagccacac   1620
cctagggttg gccaatctac tcccaggagc agggagggca ggagccaggg ctgggcataa   1680
aagtcagggc agagccatct attgcttaca tttgcttctg acacaactgt gttcactagc   1740
aacctcaaac agacacgatc ctgagaactt cagggtgagt ctatgggacc cttgatgttt   1800
tctttcccct tcttttctat ggttaagttc atgtcatagg aaggggagaa gtaacagggt   1860
acagtttaga atgggaaaca gacgaatgat tgcatcagtg tggaagtctc aggatcgttt   1920
tagtttcttt tatttgctgt tcataacaat tgttttcttt tgtttaattc ttgctttctt   1980
ttttttctt ctccgcaatt tttactatta tacttaatgc cttaacattg tgtataacaa   2040
aaggaaatat ctctgagata cattaagtaa cttaaaaaaa aactttacac agtctgccta   2100
gtacattact atttggaata tatgtgtgct tatttgcata ttcataatct ccctacttta   2160
ttttctttta tttttaattg atacataatc attatacata tttatgggtt aaagtgtaat   2220
gttttaatat gtgtacacat attgaccaaa tcagggtaat tttgcatttg taattttaaa   2280
aaatgctttc ttcttttaat atactttttt gtttatctta tttctaatac tttccctaat   2340
ctctttcttt cagggcaata atgatacaat gtatcatgcc tctttgcacc attctaaaga   2400
ataacagtga taatttctgg gttaaggcaa tagcaatatt tctgcatata aatatttctg   2460
catataaatt gtaactgatg taagaggttt catattgcta atagcagcta caatccagct   2520
accattctgc ttttatttta tggttgggat aaggctggat tattctgagt ccaagctagg   2580
ccctttttgct aatcatgttc atacctctta tcttcctccc acagctcctg ggcaacgtgc   2640
tggtctgtgt gctggcccat cactttggca aagaattcac ccctgaggtg caggcttcct   2700
ggcagaagat ggtgactgca gtggccagtg ccctgtcctc cagataccac tgagcctctt   2760
gcccatgatt cagagctttc aaggataggc tttattctgc aagcaataca aataataaat   2820
ctattctgct gagagatcac acatgatttt cttcagctct tttttttaca tctttttaaa   2880
tatatgagcc acaaagggtt tatattgagg gaagtgtgta tgtgtatttc tgcatgcctg   2940
tttgtgtttg tggtgtgtgc atgctcctca tttattttta tatgagatgt gcattttgat   3000
gagcaaataa aagcagtaaa gacacttgta cacgggagtt ctgcaagtgg gagtaaatgg   3060
tgttggagaa atccggtggg aagaaagacc tctataggac aggacttctc agaaacagat   3120
gttttggaag agatgggaaa aggttcagtg aagacctggg ggctggattg attgcagctg   3180
agtagcaagg atggttctta atgaagggaa agtgttccag ctagcgtgct agtctcccgg   3240
aactatcact ctttcacagt ctgctttgga aggactgggc ttagtatgaa aagttaggac   3300
tgagaagaat ttgaaagggg gctttttgta gcttgatatt cactactgtc ttattaccct   3360
atcataggcc caccccaaat ggaagtccca ttcttcctca ggatgtttaa gattagcatt   3420
caggaagaga tcagaggtct gctggctccc ttatcatgtc ccttatggtg cttctggcta   3480
```

-continued

```
gcgatatcac cggtat                                                 3496


<210> SEQ ID NO 2
<211> LENGTH: 3916
<212> TYPE: DNA
<213> ORGANISM: Homo sapiens

<400> SEQUENCE: 2

cgatgaagct tcctcgaggc agaagagtca agcatttgcc taaggtcgga catgtcagag    60

gcagtgccag acctatgtga gactctgcag ctactgctca tgggccctgt gctgcactga   120

tgaggaggat cagatggatg ggcaatgaa gcaaaggaat cattctgtgg ataaaggaga   180

cagccatgaa gaagtctatg actgtaaatt tgggagcagg agtctctaag gacttggatt   240

tcaaggaatt ttgactcagc aaacacaaga ccctcacggt gactttgcga gctggtgtgc   300

cagatgtgtc tatcagaggt tccagggagg gtggggtggg gtcagggctg gccaccagct   360

atcagggccc agatgggtta taggctggca ggctcagata ggtggttagg tcaggttggt   420

ggtgctgggt ggagtccatg actcccagga gccaggagag atagaccatg agtagagggc   480

agacatggga aaggtggggg aggcacagca tagcagcatt tttcattcta ctactacatg   540

ggactgctcc cctatacccc cagctagggg caagtgcctt gactcctatg ttttcaggat   600

catcatctat aaagtaagag taataattgt gtctatctca tagggttatt atgaggatca   660

aaggagatgc acactctctg gaccagtggc ctaacagttc aggacagagc tatgggcttc   720

ctatgtatgg gtcagtggtc tcaatgtagc aggcaagttc cagaagatag catcaaccac   780

tgttagagat atactgccag tctcagagcc tgatgttaat ttagcaatgg gctgggaccc   840

tcctccagta gaaccttcta accagcctcg agggactagt cggtaccgtc gacaacctcc   900

tatttgacac cactgattac cccattgata gtcacacttt gggttgtaag tgacttttta   960

tttatttgta tttttgactg cattaagagg tctctagttt tttatctctt gtttcccaaa  1020

acctaataag taactaatgc acagagcaca ttgatttgta tttattctat ttttagacat  1080

aatttattag catgcatgag caaattaaga aaaacaacaa caaatgaatg catatatatg  1140

tatatgtatg tgtgtatata tacacatata tatatatatt ttttttcttt tcttaccaga  1200

aggttttaat ccaaataagg agaagatatg cttagaactg aggtagagtt ttcatccatt  1260

ctgtcctgta agtattttgc atattctgga gacgcaggaa gagatccatc tacatatccc  1320

aaagctgaat tatggtagac aaagctcttc cacttttagt gcatcaattt cttatttgtg  1380

taataagaaa attgggaaaa cgatcttcaa tatgcttacc aagctgtgat tccaaatatt  1440

acgtaaatac acttgcaaag gaggatgttt ttagtagcaa tttgtactga tggtatgggg  1500

ccaagagata tatcttagag ggagggctga gggtttgaag tccaactcct aagccagtgc  1560

cagaagagcc aaggacaggt acggctgtca tcacttagac ctcaccctgt ggagccacac  1620

cctagggttg gccaatctac tcccaggagc agggagggca ggagccaggg ctgggcataa  1680

aagtcagggc agagccatct attgcttaca tttgcttctg acacaactgt gttcactagc  1740

aacctcaaac agacaccatg ggtcatttca cagaggagga caaggctact atcacaagcc  1800

tgtggggcaa ggtgaatgtg gaagatgctg gaggagaaac cctgggaagg taggctctgg  1860

tgaccaggac aagggaggga aggaaggacc ctgtgcctgg caaaagtcca ggtcgcttct  1920

caggatttgt ggcaccttct gactgtcaaa ctgttcttgt caatctcaca ggctcctggt  1980

tgtctaccca tggacccaga ggttctttga cagctttggc aacctgtcct ctgcctctgc  2040

catcatgggc aaccccaaag tcaaggcaca tggcaagaag gtgctgactt ccttgggaga  2100
```

-continued

```
tgccataaag cacctggatg atctcaaggg cacctttgcc cagctgagtg aactgcactg   2160

tgacaagctg catgtggatc ctgagaactt cagggtgagt ctatgggacc cttgatgttt   2220

tctttcccct tcttttctat ggttaagttc atgtcatagg aaggggagaa gtaacagggt   2280

acagtttaga atgggaaaca gacgaatgat tgcatcagtg tggaagtctc aggatcgttt   2340

tagtttcttt tatttgctgt tcataacaat tgttttcttt tgtttaattc ttgctttctt   2400

tttttttctt ctccgcaatt tttactatta tacttaatgc cttaacattg tgtataacaa   2460

aaggaaatat ctctgagata cattaagtaa cttaaaaaaa aactttacac agtctgccta   2520

gtacattact atttggaata tatgtgtgct tatttgcata ttcataatct ccctacttta   2580

ttttctttta tttttaattg atacataatc attatacata tttatgggtt aaagtgtaat   2640

gttttaatat gtgtacacat attgaccaaa tcagggtaat tttgcatttg taattttaaa   2700

aaatgctttc ttcttttaat atactttttt gtttatctta tttctaatac tttccctaat   2760

ctctttcttt cagggcaata atgatacaat gtatcatgcc tctttgcacc attctaaaga   2820

ataacagtga taatttctgg gttaaggcaa tagcaatatt tctgcatata aatatttctg   2880

catataaatt gtaactgatg taagaggttt catattgcta atagcagcta caatccagct   2940

accattctgc ttttatttta tggttgggat aaggctggat tattctgagt ccaagctagg   3000

cccttttgct aatcatgttc atacctctta tcttcctccc acagctcctg ggcaacgtgc   3060

tggtctgtgt gctggcccat cactttggca aagaattcac ccctgaggtg caggcttcct   3120

ggcagaagat ggtgactgca gtggccagtg ccctgtcctc cagataccac tgagcctctt   3180

gcccatgatt cagagctttc aaggataggc tttattctgc aagcaataca aataataaat   3240

ctattctgct gagagatcac acatgatttt cttcagctct tttttttaca tctttttaaa   3300

tatatgagcc acaaagggtt tatattgagg gaagtgtgta tgtgtatttc tgcatgcctg   3360

tttgtgtttg tggtgtgtgc atgctcctca tttattttta tatgagatgt gcattttgat   3420

gagcaaataa aagcagtaaa gacacttgta cacgggagtt ctgcaagtgg gagtaaatgg   3480

tgttggagaa atccggtggg aagaaagacc tctataggac aggacttctc agaaacagat   3540

gttttggaag agatgggaaa aggttcagtg aagacctggg ggctggattg attgcagctg   3600

agtagcaagg atggttctta atgaagggaa agtgttccag ctagcgtgct agtctcccgg   3660

aactatcact ctttcacagt ctgctttgga aggactgggc ttagtatgaa aagttaggac   3720

tgagaagaat ttgaaagggg gctttttgta gcttgatatt cactactgtc ttattaccct   3780

atcataggcc caccccaaat ggaagtccca ttcttcctca ggatgtttaa gattagcatt   3840

caggaagaga tcagaggtct gctggctccc ttatcatgtc ccttatggtg cttctggcta   3900

gcgatatcac cggtat                                                   3916
```

<210> SEQ ID NO 3
<211> LENGTH: 3385
<212> TYPE: DNA
<213> ORGANISM: Homo sapiens

<400> SEQUENCE: 3

```
cgatgaagct tcctcgaggc agaagagtca agcatttgcc taaggtcgga catgtcagag     60

gcagtgccag acctatgtga gactctgcag ctactgctca tgggccctgt gctgcactga    120

tgaggaggat cagatggatg gggcaatgaa gcaaaggaat cattctgtgg ataaaggaga    180

cagccatgaa gaagtctatg actgtaaatt tgggagcagg agtctctaag gacttggatt    240
```

-continued

```
tcaaggaatt ttgactcagc aaacacaaga ccctcacggt gactttgcga gctggtgtgc    300
cagatgtgtc tatcagaggt tccagggagg gtggggtggg gtcagggctg gccaccagct    360
atcagggccc agatgggtta taggctggca ggctcagata ggtggttagg tcaggttggt    420
ggtgctgggt ggagtccatg actcccagga gccaggagag atagaccatg agtagagggc    480
agacatggga aaggtggggg aggcacagca tagcagcatt tttcattcta ctactacatg    540
ggactgctcc cctatacccc cagctagggg caagtgcctt gactcctatg ttttcaggat    600
catcatctat aaagtaagag taataattgt gtctatctca tagggttatt atgaggatca    660
aaggagatgc acactctctg gaccagtggc ctaacagttc aggacagagc tatgggcttc    720
ctatgtatgg gtcagtggtc tcaatgtagc aggcaagttc cagaagatag catcaaccac    780
tgttagagat atactgccag tctcagagcc tgatgttaat ttagcaatgg gctgggaccc    840
tcctccagta gaaccttcta accagcctcg agggactagt cggtaccgat ttatttcaaa    900
taggtacgga taagtagata ttgaggtaag cattaggtct tatattatgt aacactaatc    960
tattactgcg ctgaaactgt ggtctttatg aaaattgttt tcactacact attgagaaat   1020
taagagataa tggcaaaagt cacaaagagt atattcaaaa agaagtatag cactttttcc   1080
ttagaaacca ctgctaactg aaagagacta agatttgtcc cgtcaaaaat cctggaccta   1140
tgcctaaaac acatttcaca atccctgaac ttttcaaaaa ttggtacatg ctttagcttt   1200
aaactacagg cctcactgga gctacagaca agaaggtaaa aaacggctga caaaagaagt   1260
cctggtatcc tctatgatgg gagaaggaaa ctagctaaag ggaagaataa attagagaaa   1320
aactggaatg actgaatcgg aacaaggcaa aggctataaa aaaaattaag cagcagtatc   1380
ctcttggggg ccccttcccc acactatctc aatgcaaata tctgtctgaa acggtccctg   1440
gctaaactcc acccatgggt tggccagcct tgccttgacc aatagccttg acaaggcaaa   1500
cttgaccaat agtcttagag tatccagtga ggccaggggc cggcggctgg ctagggatga   1560
agaataaaag gaagcaccct tcagcagttc cacacactcg cttctggaac gtctgagatt   1620
atcaataagc tcctagtcca gacgcgatcc tgagaacttc agggtgagtc tatgggaccc   1680
ttgatgtttt ctttcccctt cttttctatg gttaagttca tgtcatagga aggggagaag   1740
taacagggta cagtttagaa tgggaaacag acgaatgatt gcatcagtgt ggaagtctca   1800
ggatcgtttt agtttctttt atttgctgtt cataacaatt gttttctttt gtttaattct   1860
tgctttcttt ttttttcttc tccgcaattt ttactattat acttaatgcc ttaacattgt   1920
gtataacaaa aggaaatatc tctgagatac attaagtaac ttaaaaaaaa actttacaca   1980
gtctgcctag tacattacta tttggaatat atgtgtgctt atttgcatat tcataatctc   2040
cctactttat tttcttttat ttttaattga tacataatca ttatacatat ttatgggtta   2100
aagtgtaatg ttttaatatg tgtacacata ttgaccaaat cagggtaatt ttgcatttgt   2160
aattttaaaa aatgctttct tcttttaata tacttttttg tttatcttat ttctaatact   2220
ttccctaatc tctttctttc agggcaataa tgatacaatg tatcatgcct ctttgcacca   2280
ttctaaagaa taacagtgat aatttctggg ttaaggcaat agcaatattt ctgcatataa   2340
atatttctgc atataaattg taactgatgt aagaggtttc atattgctaa tagcagctac   2400
aatccagcta ccattctgct tttattttat ggttgggata aggctggatt attctgagtc   2460
caagctaggc ccttttgcta atcatgttca tacctcttat cttcctccca cagctcctgg   2520
gcaacgtgct ggtctgtgtg ctggcccatc actttggcaa agaattcacc cctgaggtgc   2580
aggcttcctg gcagaagatg gtgactgcag tggccagtgc cctgtcctcc agataccact   2640
```

```
gagcctcttg cccatgattc agagctttca aggataggct ttattctgca agcaatacaa   2700

ataataaatc tattctgctg agagatcaca catgattttc ttcagctctt ttttttacat   2760

ctttttaaat atatgagcca caaagggttt atattgaggg aagtgtgtat gtgtatttct   2820

gcatgcctgt ttgtgtttgt ggtgtgtgca tgctcctcat ttatttttat atgagatgtg   2880

cattttgatg agcaaataaa agcagtaaag acacttgtac acgggagttc tgcaagtggg   2940

agtaaatggt gttggagaaa tccggtggga agaaagacct ctataggaca ggacttctca   3000

gaaacagatg ttttggaaga gatgggaaaa ggttcagtga agacctgggg gctggattga   3060

ttgcagctga gtagcaagga tggttcttaa tgaagggaaa gtgttccagc tagcgtgcta   3120

gtctcccgga actatcactc tttcacagtc tgctttggaa ggactgggct tagtatgaaa   3180

agttaggact gagaagaatt tgaaaggggg ctttttgtag cttgatattc actactgtct   3240

tattacccta tcataggccc accccaaatg gaagtcccat tcttcctcag gatgtttaag   3300

attagcattc aggaagagat cagaggtctg ctggctccct tatcatgtcc cttatggtgc   3360

ttctggctag cgatatcacc ggtat                                         3385
```

<210> SEQ ID NO 4
<211> LENGTH: 3805
<212> TYPE: DNA
<213> ORGANISM: Homo sapiens

<400> SEQUENCE: 4

```
cgatgaagct tcctcgaggc agaagagtca agcatttgcc taaggtcgga catgtcagag     60

gcagtgccag acctatgtga gactctgcag ctactgctca tgggccctgt gctgcactga    120

tgaggaggat cagatggatg gggcaatgaa gcaaaggaat cattctgtgg ataaaggaga    180

cagccatgaa gaagtctatg actgtaaatt tgggagcagg agtctctaag gacttggatt    240

tcaaggaatt ttgactcagc aaacacaaga ccctcacggt gactttgcga gctggtgtgc    300

cagatgtgtc tatcagaggt tccagggagg gtggggtggg gtcagggctg gccaccagct    360

atcagggccc agatgggtta taggctggca ggctcagata ggtggttagg tcaggttggt    420

ggtgctgggt ggagtccatg actcccagga gccaggagag atagaccatg agtagagggc    480

agacatggga aaggtggggg aggcacagca tagcagcatt tttcattcta ctactacatg    540

ggactgctcc cctataccccc cagctagggg caagtgcctt gactcctatg ttttcaggat    600

catcatctat aaagtaagag taataattgt gtctatctca tagggttatt atgaggatca    660

aaggagatgc acactctctg gaccagtggc ctaacagttc aggacagagc tatgggcttc    720

ctatgtatgg gtcagtggtc tcaatgtagc aggcaagttc cagaagatag catcaaccac    780

tgttagagat atactgccag tctcagagcc tgatgttaat ttagcaatgg gctgggaccc    840

tcctccagta gaaccttcta accagcctcg agggactagt cggtaccgat ttatttcaaa    900

taggtacgga taagtagata ttgaggtaag cattaggtct tatattatgt aacactaatc    960

tattactgcg ctgaaactgt ggtctttatg aaaattgttt tcactacact attgagaaat   1020

taagagataa tggcaaaagt cacaaagagt atattcaaaa agaagtatag cactttttcc   1080

ttagaaacca ctgctaactg aaagagacta agatttgtcc cgtcaaaaat cctggaccta   1140

tgcctaaaac acatttcaca atccctgaac ttttcaaaaa ttggtacatg ctttagcttt   1200

aaactacagg cctcactgga gctacagaca agaaggtaaa aaacggctga caaaagaagt   1260

cctggtatcc tctatgatgg gagaaggaaa ctagctaaag ggaagaataa attagagaaa   1320
```

-continued

```
aactggaatg actgaatcgg aacaaggcaa aggctataaa aaaaattaag cagcagtatc   1380
ctcttggggg ccccttcccc acactatctc aatgcaaata tctgtctgaa acggtccctg   1440
gctaaactcc acccatgggt tggccagcct tgccttgacc aatagccttg acaaggcaaa   1500
cttgaccaat agtcttagag tatccagtga ggccaggggc cggcggctgg ctagggatga   1560
agaataaaag gaagcaccct tcagcagttc cacacactcg cttctggaac gtctgagatt   1620
atcaataagc tcctagtcca gacgccatgg gtcatttcac agaggaggac aaggctacta   1680
tcacaagcct gtggggcaag gtgaatgtgg aagatgctgg aggagaaacc ctgggaaggt   1740
aggctctggt gaccaggaca agggagggaa ggaaggaccc tgtgcctggc aaaagtccag   1800
gtcgcttctc aggatttgtg gcaccttctg actgtcaaac tgttcttgtc aatctcacag   1860
gctcctggtt gtctacccat ggacccagag gttctttgac agctttggca acctgtcctc   1920
tgcctctgcc atcatgggca accccaaagt caaggcacat ggcaagaagg tgctgacttc   1980
cttgggagat gccataaagc acctggatga tctcaagggc acctttgccc agctgagtga   2040
actgcactgt gacaagctgc atgtggatcc tgagaacttc agggtgagtc tatgggaccc   2100
ttgatgtttt ctttcccctt cttttctatg gttaagttca tgtcatagga aggggagaag   2160
taacagggta cagtttagaa tgggaaacag acgaatgatt gcatcagtgt ggaagtctca   2220
ggatcgtttt agtttctttt atttgctgtt cataacaatt gttttctttt gtttaattct   2280
tgctttcttt ttttttcttc tccgcaattt ttactattat acttaatgcc ttaacattgt   2340
gtataacaaa aggaaatatc tctgagatac attaagtaac ttaaaaaaaa actttacaca   2400
gtctgcctag tacattacta tttggaatat atgtgtgctt atttgcatat tcataatctc   2460
cctactttat tttcttttat ttttaattga tacataatca ttatacatat ttatgggtta   2520
aagtgtaatg ttttaatatg tgtacacata ttgaccaaat cagggtaatt ttgcatttgt   2580
aattttaaaa aatgctttct tcttttaata tactttttttg tttatcttat ttctaatact   2640
ttccctaatc tctttctttc agggcaataa tgatacaatg tatcatgcct ctttgcacca   2700
ttctaaagaa taacagtgat aatttctggg ttaaggcaat agcaatattt ctgcatataa   2760
atatttctgc atataaattg taactgatgt aagaggtttc atattgctaa tagcagctac   2820
aatccagcta ccattctgct tttattttat ggttgggata aggctggatt attctgagtc   2880
caagctaggc ccttttgcta atcatgttca tacctcttat cttcctccca cagctcctgg   2940
gcaacgtgct ggtctgtgtg ctggcccatc actttggcaa agaattcacc cctgaggtgc   3000
aggcttcctg gcagaagatg gtgactgcag tggccagtgc cctgtcctcc agataccact   3060
gagcctcttg cccatgattc agagctttca aggataggct ttattctgca agcaatacaa   3120
ataataaatc tattctgctg agagatcaca catgattttc ttcagctctt tttttttacat   3180
ctttttaaat atatgagcca caaagggttt atattgaggg aagtgtgtat gtgtatttct   3240
gcatgcctgt ttgtgtttgt ggtgtgtgca tgctcctcat ttatttttat atgagatgtg   3300
cattttgatg agcaaataaa agcagtaaag acacttgtac acgggagttc tgcaagtggg   3360
agtaaatggt gttggagaaa tccggtggga agaaagacct ctataggaca ggacttctca   3420
gaaacagatg ttttggaaga gatgggaaaa ggttcagtga agacctgggg gctggattga   3480
ttgcagctga gtagcaagga tggttcttaa tgaagggaaa gtgttccagc tagcgtgcta   3540
gtctcccgga actatcactc tttcacagtc tgctttggaa ggactgggct tagtatgaaa   3600
agttaggact gagaagaatt tgaaaggggg ctttttgtag cttgatattc actactgtct   3660
tattacccta tcataggccc accccaaatg gaagtcccat tcttcctcag gatgtttaag   3720
```

-continued

```
attagcattc aggaagagat cagaggtctg ctggctccct tatcatgtcc cttatggtgc    3780

ttctggctag cgatatcacc ggtat                                          3805
```